(12) United States Patent
Hakansson et al.

(10) Patent No.: US 11,430,560 B2
(45) Date of Patent: Aug. 30, 2022

(54) EXTRACORPOREAL BLOOD TREATMENT SYSTEM AND METHOD INCLUDING USER-INTERACTABLE SETTINGS

(71) Applicant: GAMBRO LUNDIA AB, Lund (SE)

(72) Inventors: Annmargret Hakansson, Kagerod (SE); Bendik Torvin, Schaanwald (LI); Maria Johnsson, Malmo (SE); Par-Olof Hakansson, Vellinge (SE); Roger Nilsson, Hoor (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 16/309,221

(22) PCT Filed: Jun. 27, 2017

(86) PCT No.: PCT/EP2017/065766
§ 371 (c)(1),
(2) Date: Dec. 12, 2018

(87) PCT Pub. No.: WO2018/001993
PCT Pub. Date: Jan. 4, 2018

(65) Prior Publication Data
US 2019/0198152 A1  Jun. 27, 2019

(30) Foreign Application Priority Data

Jun. 30, 2016 (SE) .................... 1650947-3

(51) Int. Cl.
*G16H 20/40* (2018.01)
*G16H 40/63* (2018.01)
(Continued)

(52) U.S. Cl.
CPC ............ *G16H 20/40* (2018.01); *A61M 1/267* (2014.02); *G06F 3/0482* (2013.01);
(Continued)

(58) Field of Classification Search
CPC .. A61M 1/267; G06F 3/04815; G06F 3/0482; G06F 3/04847; G06F 3/0488; G16H 20/40; G16H 20/63; G06Q 50/22–24
(Continued)

(56) References Cited

U.S. PATENT DOCUMENTS 5,609,770 A * 3/1997 Zimmerman ........... A61M 1/16
210/739
6,738,052 B1    5/2004 Manke
(Continued)

FOREIGN PATENT DOCUMENTS

WO     WO 98/35747       8/1998
WO     WO 2008/074316    6/2008
(Continued)

OTHER PUBLICATIONS

PCT Search Report and Written Opinion for PCT/EP2017/065762 dated Aug. 31, 2017 (14 pages).
(Continued)

*Primary Examiner* — Jason S Tiedeman
*Assistant Examiner* — Jessica Marie Webb
(74) *Attorney, Agent, or Firm* — Mueting Raasch Group

(57) ABSTRACT

Graphical user interfaces for use with extracorporeal blood treatment systems may include a plurality of displayable settings cards. The plurality of settings cards may be grouped or arranged into a card set and a plurality of card subsets. Each of the card set and the plurality of card subsets may be displayable as a stack of settings cards with at least one settings card presented at the forefront of the stack to a user. Further, each settings card of the plurality of settings cards may also be displayed by itself.

29 Claims, 12 Drawing Sheets

(51) Int. Cl.
  *G06F 3/0482* (2013.01)
  *G06F 3/04847* (2022.01)
  *G06F 3/0488* (2022.01)
  *G06F 3/04815* (2022.01)
  *G06F 3/04886* (2022.01)
  *A61M 1/26* (2006.01)
  *G06F 3/044* (2006.01)

(52) U.S. Cl.
  CPC ........ *G06F 3/0488* (2013.01); *G06F 3/04815* (2013.01); *G06F 3/04847* (2013.01); *G16H 40/63* (2018.01); *A61M 2205/502* (2013.01); *A61M 2205/505* (2013.01); *G06F 3/044* (2013.01); *G06F 3/04886* (2013.01)

(58) Field of Classification Search
  USPC .......................................................... 705/2
  See application file for complete search history.

(56) References Cited

U.S. PATENT DOCUMENTS

| | | | | |
|---|---|---|---|---|
| 8,438,504 | B2* | 5/2013 | Cranfill | G06F 9/451 |
| | | | | 715/863 |
| 9,001,047 | B2* | 4/2015 | Forstall | G06F 3/04845 |
| | | | | 345/173 |
| 9,830,056 | B1* | 11/2017 | Keely | G06F 3/04883 |
| 10,168,826 | B2* | 1/2019 | Bernstein | G06F 3/0483 |
| 2005/0045540 | A1 | 3/2005 | Connell | |
| 2005/0070837 | A1 | 3/2005 | Ferrarini | |
| 2005/0256444 | A1 | 11/2005 | O'Mahony | |
| 2008/0249377 | A1 | 10/2008 | Molducci | |
| 2011/0093481 | A1* | 4/2011 | Hussam | G06F 16/20 |
| | | | | 707/756 |
| 2011/0291945 | A1* | 12/2011 | Ewing, Jr. | G06F 1/1686 |
| | | | | 345/173 |
| 2012/0079419 | A1* | 3/2012 | Ajitomi | G06F 9/451 |
| | | | | 715/781 |
| 2012/0138533 | A1 | 6/2012 | Curtis | |
| 2013/0018355 | A1* | 1/2013 | Brand | G16H 40/67 |
| | | | | 604/500 |
| 2013/0047115 | A1* | 2/2013 | Migos | G06F 3/0484 |
| | | | | 715/776 |
| 2013/0145291 | A1* | 6/2013 | Weber | G06F 3/0483 |
| | | | | 715/760 |
| 2013/0185642 | A1* | 7/2013 | Gammons | G06F 3/0482 |
| | | | | 715/733 |
| 2013/0190717 | A1* | 7/2013 | Dollar | A61M 1/3664 |
| | | | | 604/505 |
| 2013/0257878 | A1* | 10/2013 | Jin | G06T 13/00 |
| | | | | 345/473 |
| 2013/0346901 | A1* | 12/2013 | Diaz | G16H 40/63 |
| | | | | 715/771 |
| 2014/0099235 | A1* | 4/2014 | Ellingboe | A61M 1/3626 |
| | | | | 422/45 |
| 2014/0333530 | A1 | 11/2014 | Agnetta | |
| 2015/0227293 | A1 | 8/2015 | Stenquist | |
| 2016/0246375 | A1* | 8/2016 | Rihn | G06F 3/04886 |
| 2016/0303303 | A1* | 10/2016 | Rovatti | A61M 1/1601 |
| 2016/0310656 | A1* | 10/2016 | Vinci | A61M 1/3434 |
| 2017/0083171 | A1* | 3/2017 | Nelson | G06F 16/9535 |
| 2017/0239412 | A1* | 8/2017 | Court | H04W 76/15 |
| 2017/0326284 | A1* | 11/2017 | Dulsner | G16H 40/63 |

FOREIGN PATENT DOCUMENTS

| | | | |
|---|---|---|---|
| WO | WO 2014/033119 | 3/2014 | |
| WO | WO 2014/105516 | 7/2014 | |
| WO | WO 2014/105517 | 7/2014 | |
| WO | WO 2016/089741 | 6/2016 | |
| WO | WO-2016089741 A1 * | 6/2016 | ......... G06F 19/3481 |

OTHER PUBLICATIONS

PCT Search Report and Written Opinion for PCT/EP2017/065766 dated Aug. 21, 2017 (13 pages).

* cited by examiner

EXTRACORPOREAL BLOOD TREATMENT SYSTEM AND METHOD INCLUDING USER-INTERACTABLE SETTINGS

This application is a U.S. National Stage Application of International Application No. PCT/EP2017/065766 filed 27 Jun. 2017 and published in English on 4 Jan. 2018 as International Publication No. WO 2018/001993 A1, which claims the benefit of priority under 35 U.S.C. § 119(a) of Swedish Patent Application No. 1650947-3 filed 30 Jun. 2016, each of which are incorporated herein by reference in their entireties.

The disclosure herein relates to medical treatment apparatus. More particularly, the disclosure relates to systems and methods for use in providing graphical user interfaces related to medical treatment apparatus such as extracorporeal blood treatment apparatus.

Medical treatment apparatus often includes a graphical user interface depicted on a display. A user may use the graphical user interface to, among other things, configure and setup a treatment, monitor and perform a treatment, and perform various post-treatment processes. The graphical user interface for treatment apparatus may include a plurality of different graphical elements, graphical regions, and graphical areas configured for performing the functionality associated with the treatment apparatus.

Medical treatment apparatus may be configured to perform extracorporeal blood treatment. Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating such undesirable matter from their blood, for example, in the case of a patient who is suffering from temporary or permanent kidney failure. These and other patients may, for instance, undergo extracorporeal blood treatment to add to or to eliminate matter from their blood, to maintain an acid-base balance, and/or to eliminate excess body fluids.

SUMMARY

The exemplary systems and methods may be described as overcoming usability barriers and offering a user-friendly graphical user interface. For example, the graphical user interface may "open up" how a blood treatment may be structured, visualized, and interacted with or operated. The exemplary systems and methods may include grouping specific settings on "pages" or "cards," and may enable users to "swipe" between pages or cards and/or access the pages or cards directly via shortcuts. The exemplary systems and methods may be described as resulting in a unique and user-friendly way to navigate and adjust a plurality of settings and subsettings. Further, the exemplary "pages" or "cards" and settings located thereon actively contribute to the interaction between various process features and/or settings of the graphical user interface and the computing apparatus by improving the interaction between the users and the various process features and/or settings of the graphical user interface, which, in turn, improves the interaction between the various process features and/or settings of the graphical user interface and the computing apparatus. For example, the exemplary "pages" or "cards" may be described as actively improving the usability of the interaction between the various process features and/or settings of the graphical user interface and the computing apparatus because users may be able to access such various process features and/or settings in a more user-friendly way than previous graphical user interfaces.

Current deficiencies of touch screen graphical users interfaces exist, and tendencies may exist within the field of medical treatments to make the navigation and adjustment of settings overly complex such that, e.g., the graphical user interfaces may even intimidate users/operators. For example, graphical user interfaces may be crowded with information that is badly structured and scattered with numbers and symbols. Further, for example, it may be very difficult, especially for novice users, to get a simple overview of how a treatment is "set up" and to determine where different settings can be found. Still further, graphical user interfaces may present too many settings at the same time, which may lead to complex structures making navigation and orientation unnecessarily difficult and overwhelming.

The exemplary systems and methods may be described as providing an overview of settings or subsettings and having an intuitive navigation (e.g., being able to locate and change desired settings quickly with a sense of control and orientation and minimum effort and disorientation). The exemplary systems and methods may use individual "cards" to present groups of settings. The cards may enable users to group certain settings in their own way. Such groupings of settings can be ultrafiltration settings, dialysis fluid settings, time settings, treatment modalities, etc. Further, each of the settings cards may include further access to subsettings such as, e.g., ultrafiltration profiling from the ultrafiltration settings card, etc. The arrangement and groupings of the settings cards as well as the additional functionality of the exemplary systems and methods described further herein may improve the interaction between the settings and processes of the graphical user interface and the computing apparatus because users may be able to more intuitively navigate such settings and subsettings located in and grouped within various settings cards, which in turn, will improve the interaction between such settings and subsettings and computing apparatus.

The exemplary systems and methods may gather all settings in a stack of cards. The stack of cards may provide a "shallow depth" of interaction and may prevent users from getting lost in "deep" levels of interaction and confusing settings folder structures. By using card stacks, users may easily "flick through" the stack of cards (e.g., swipe sideways) to find the desired settings, which may be described as providing a clear, natural, and expedient process, or way, to find settings.

Further, the order in which the cards are placed, or arranged, within the stack may be dependent on the expected user sequence. The sequence can be rearranged by every clinic to accommodate each clinic's preferred order of performing tasks, or doing things, because, e.g., clinics often have different procedures, different processes, different treatments, etc. Still further, the settings cards that are available to a user may be different for each clinic. For instance, different sets or subsets of cards may be configured to different clinics, e.g., depending on the type of treatments the clinics provide, etc. For example, sodium profiling may be used by a particular clinic, and thus, a system configured for this clinic may include a set of cards including a sodium profiling settings card. Other clinics, which may not use, or may not be authorized to use, sodium profiling may have systems that are configured to include a set of cards that does not include, or excludes, the sodium profiling settings card. In other words, certain settings cards may be forbidden depending on the setting where the system may be used. Further, for example, when a blood treatment is being performed at a patient's home, the system may be configured to only display, or include, the settings cards that are relevant the particular patient's treatment. In other words, settings cards that are not relevant to a patient's treatment may be excluded, or not shown by, the system. In essence, the set of all settings cards may be pre-determined for particular systems to be used in particular settings or with particular patients for, e.g., ease of use, lack of clutter, less confusion, etc.

The exemplary systems and methods further provide a grouping of settings cards in a supportive way by, e.g., utilizing how a workflow of a treatment is generally understood. For example, a treatment session may include the following phrases: "Before Treatment" (e.g., setup and priming); "During Treatment" (e.g., prescription, medication, profiling, rinseback); and "After Treatment" (e.g., disinfection). By organizing the cards in groups based on these three phases, the exemplary systems and methods may present settings cards that are only relevant at each specific phase. For example, the exemplary systems and methods may depict three icons/shortcuts on the main graphical user interface configured for accessing each of these groups. So, for example, if a user selects, or presses, the shortcut for the "Setup and Priming," the settings cards relevant to setup and priming such as, e.g., treatment mode, consumables & priming, etc. may be displayed in a stack. Further, which cards belong in which phase, or perhaps in several, may be preset, or configured, by a user (e.g., a clinic head nurse or technician.)

A user may also be able to access individual cards directly (e.g., without flicking through a stack of cards) by selecting, or pressing, related process feature graphical elements such as, e.g., parameter read-outs and/or settings icons on the graphical user interface. For example, data on the graphical user interface may represent shortcuts to cards in which the data or settings are located. If a user selects an ultrafiltration graphical element or segment, then the ultrafiltration card may be displayed (which is the same ultrafiltration card as is found in the stack of all settings cards or in the stack of "treatment-phase" cards). Further, if a user selects the "Remaining Time" number on the graphical user interface, the treatment time settings card may be displayed. This functionality may be described as creating familiarity and consistency in the settings cards and providing freedom to access the settings cards in different ways. The individually accessed cards might open within the stack (e.g., such that a user can flick further if you need to make changes on other cards) or as an individual card.

It may be described that the exemplary systems and methods described herein may make navigating and handling settings easy to understand, intuitive to operate, and welcoming to users. Further, the exemplary systems and methods may be described as providing, or giving, users a clearer overview of all settings, may reduce stress, and may improve patient safety, work flow, and efficiency. The exemplary systems and methods may translate to a better, more efficient working environment for operators, which may, thereby provide a safer and better treatment experience for patients. Additionally, the exemplary systems and methods may improve patient adherence by providing a more pleasant experience.

One exemplary extracorporeal blood treatment system may include extracorporeal blood treatment apparatus, a display apparatus, and a computing apparatus operatively coupled to the extracorporeal blood treatment apparatus and the display apparatus. The extracorporeal blood treatment apparatus may include one or more pumps, one or more sensors, and one or more disposable elements for use in performing an extracorporeal blood treatment. The display apparatus may include a graphical user interface configured to depict a plurality of settings cards. The computing apparatus may include one or more processors and may be configured to provide a plurality of settings cards defining a card set, and each settings card of the plurality of settings cards may be configured to display one or more settings related to one or more processes of the extracorporeal blood treatment system by the extracorporeal blood treatment apparatus. Further, the settings cards may be grouped into a plurality of card subsets, and each card subset may include a plurality of settings cards that is less settings cards than the card set. The computing apparatus may be further configured to display on the graphical user interface an all-settings graphical element and a plurality of card subset graphical elements. The all-settings graphical element may be associated with the display of the card set, and each card subset graphical element of the plurality of subset graphical elements may be associated with the display of a different card subset of the plurality of card subsets. The computing apparatus may be further configured to allow a user to select the all-settings graphical element to display a stack of the plurality of settings cards of the card set, and at least one settings card of the stack of the plurality of settings cards of the card set may be presented at the forefront of the stack to the user. The computing apparatus may be further configured to allow a user to select one of the plurality of subset graphical elements to display a stack of the plurality of settings cards of the card subset associated with the selected card subset graphical element. Further, at least one settings card of the stack of the plurality of settings cards of the selected card subset may be at the forefront of the stack to the user. The computing apparatus may be further configured to change one or more settings of the one or more processes of the extracorporeal blood treatment system performable by the extracorporeal blood treatment apparatus in response to a user modifying one or more settings of the at least one presented settings card.

One exemplary method for an extracorporeal blood treatment system may include providing extracorporeal blood treatment apparatus including one or more pumps, one or more sensors, and one or more disposable elements for use in performing an extracorporeal blood treatment. The exemplary method may further include providing a graphical user interface on a display apparatus configured to depict a plurality of settings cards and providing a plurality of settings cards defining a card set. Each settings card of the plurality of settings cards may be configured to display one or more settings related to one or more processes of the extracorporeal blood treatment system performable by the extracorporeal blood treatment apparatus, and the plurality of settings cards may be grouped into a plurality of card subsets. Further, each card subset may include a plurality of settings cards that is less settings cards than the card set. The exemplary method may further include displaying on the graphical user interface an all-settings graphical element and a plurality of card subset graphical elements. The all-settings graphical element may be associated with the display of the card set, and each card subset graphical element of the plurality of subset graphical elements may be associated with the display of a different card subset of the plurality of card subsets. The exemplary method may further include allowing a user to select the all-settings graphical element to display a stack of the plurality of settings cards of the card set. Further, at least one settings card of the stack of the plurality of settings cards of the card set may be at the forefront of the stack to the user. The exemplary method may further include allowing a user to select one of the plurality of subset graphical elements to display a stack of the plurality of settings cards of the card subset associated with the selected card subset graphical element. Further, at least one settings card of the stack of the plurality of settings cards of the selected card subset may be at the forefront of the stack to the user. The exemplary method may further include changing one or more settings of the one or more processes of the extracorporeal blood treatment system performable by the extracorporeal blood treatment apparatus in response to a user modifying one or more settings of the at least one presented settings card.

In one or more embodiments, the computing apparatus may be further configured to execute or the method may further include displaying on the graphical user interface a plurality of process feature graphical elements, and each process feature graphical element of the plurality of process feature graphical elements may correspond with a different process feature of the one or more processes of the extracorporeal blood treatment system performable by the extracorporeal blood treatment apparatus and may be associated with the display of a single settings card of the plurality of settings cards. The computing apparatus may be further configured to execute or the method may further include allowing a user to select a process feature graphical element of the plurality of process feature graphical elements to display the single settings card associated with the selected process feature graphical element and changing one or more settings of the one or more processes of the extracorporeal blood treatment system performable by the extracorporeal blood treatment apparatus in response to a user modifying one or more settings of the displayed single settings card.

In one or more embodiments, the stack of settings cards may be graphically displayed as a three-dimensional deck of settings cards. Further, the one or more settings cards presented at the forefront of the stack may be changed in response to user interaction with the graphical user interface (e.g., a user performing a gesture proximate the stack of settings cards). For example, a user may be allowed to swipe between the plurality of settings cards when displayed in a stack.

In one or more embodiments, the computing apparatus may be further configured to execute or the method may further include changing the order of the plurality of settings cards when displayed in a stack in response to user interaction with the graphical user interface. In other words, the computing apparatus may be further configured to execute or the method may further include allowing a user to select the order of the plurality of settings cards when displayed in a stack. In one or more embodiments, the computing apparatus may be further configured to execute or the method may further include configuring which settings cards of the plurality of settings cards are grouped into the plurality of card subsets in response to user interaction with the graphical user interface. In other words, the computing apparatus may be further configured to execute or the method may further include allowing a user to configure which settings cards of the plurality of settings cards are grouped into the plurality of card subsets.

In one or more embodiments, each card subset of the plurality of card subsets may be associated with a different chronological phase of a treatment process performable by the extracorporeal blood treatment system. In one or more embodiments, the plurality of card subsets may include a preparation card subset, and the preparation card subset may include a treatment mode settings card, a setup settings card, and a priming settings card. In one or more embodiments, the plurality of card subsets may include a treatment card subset, wherein the treatment card subset may include a blood settings card, an ultrafiltration settings card, a dialysis fluid settings card, and a treatment time settings card. In one or more embodiments, the plurality of card subsets may include a disinfection subset of settings cards.

In one or more embodiments, the computing apparatus may be further configured to execute or the method may further include displaying at least one settings card of the plurality of settings cards in response to a status change of one or more processes being performed. In at least one embodiment, the treatment time settings card may be displayed in response to expiration of a treatment time period.

In one or more embodiments, the one or more settings of at least one settings cards of the plurality of settings cards may be graphically expandable to display additional information with respect to the associated setting.

In one or more embodiments, the plurality of settings cards of the card set may be associated with a treatment cycle, and the computing apparatus may be further configured to execute or the method may further include providing a plurality of system configuration settings cards defining a system configuration card set different from the card set associated with a blood treatment.

In one or more embodiments, the display may include a touchscreen.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
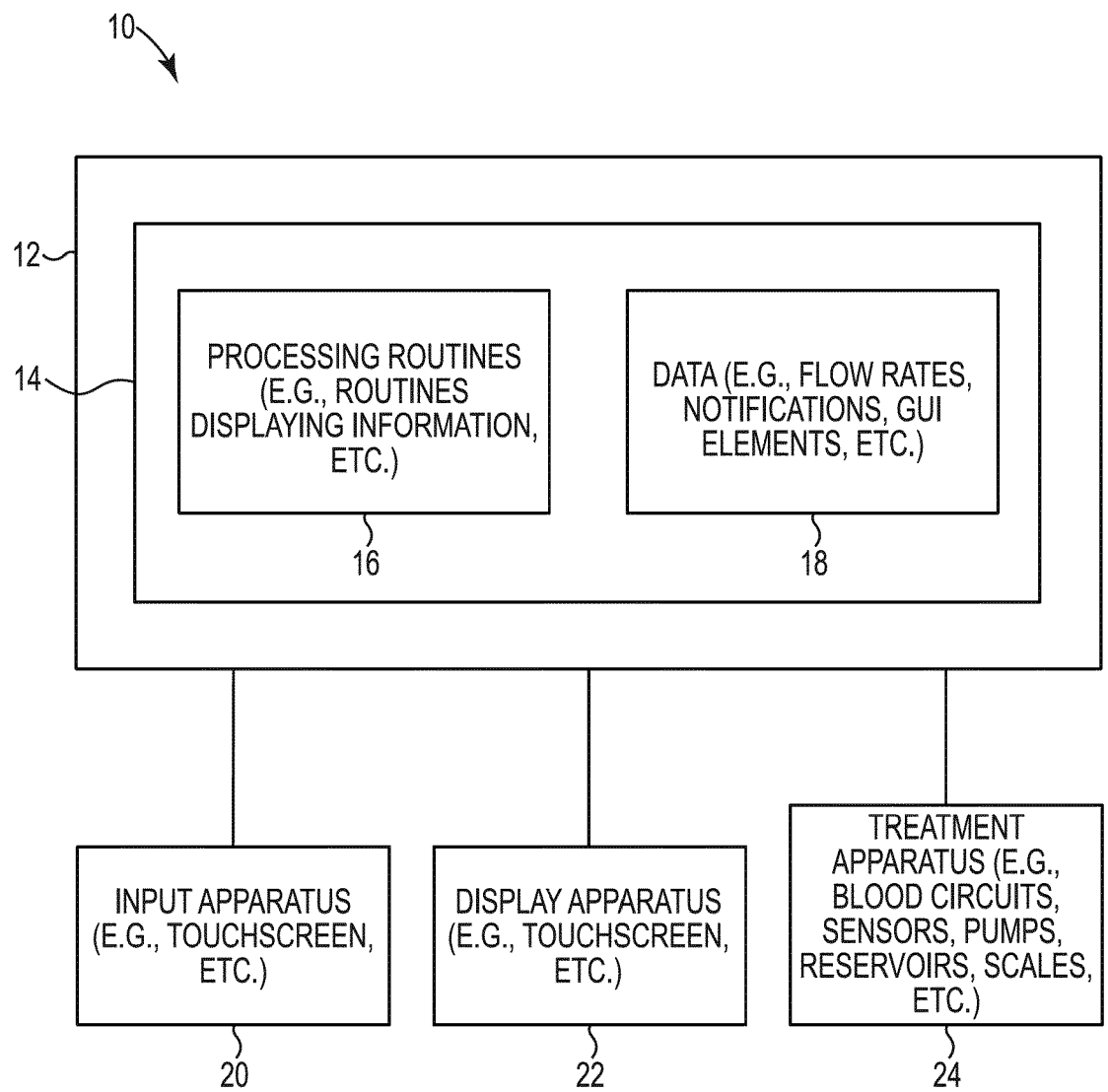
FIG. 1 is a block diagram of an exemplary medical treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary graphical user interface systems and methods for use with medical treatment apparatus such as, e.g., extracorporeal blood treatment apparatus, shall be described with reference to FIGS. 1-8. It will be apparent to one skilled in the art that elements or processes from one embodiment may be used in combination with elements or processes of the other embodiments, and that the possible embodiments of such graphical user interface systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may provide, or include, graphical user interfaces (e.g., user-interactable graphical user interfaces, graphical user interfaces depicted on single-touch or multi-touch touchscreens, etc.) that include, or depict, a plurality of graphical elements, graphical regions, and graphical areas configured to allow a user to adjust one or more settings (e.g., parameters, values, modes, etc.) with respect to one or more processes (e.g., one or more processes of an extracorporeal blood treatment system, etc.). In particular, the graphical user interfaces may include a plurality of settings cards, and each settings card of the plurality of settings cards may include one or more settings related to the one or more processes. The plurality of settings cards may be grouped into multiple groups. For example, all of the plurality of settings cards may be grouped into a card set (e.g., master card set), and some of the plurality of settings cards may be grouped into card subsets. Each of the card set and card subsets may be displayed as stacks of settings cards on the graphical user interface, and a user may "flip through" the stacks of settings cards and change one or more settings on the presented, forefront, or topmost, settings cards of the stack. The stacks of the settings cards may be resemble, or represent, a three-dimensional stack of cards such that a "topmost" card may be exposed (e.g., not obscured, etc.) while settings cards under the topmost settings card may not be exposed (e.g., may be obscured). To represent unexposed, or obscured, settings cards that are part of the card set or card subset displayed as part of a stack of the settings cards, the edges of the unexposed settings cards may be depicted proximate (e.g., to the right and/or to the left depending on which direction a "swipe" will bring such settings cards to the "top") the topmost settings card to give users the impression of a physical, three-dimensional stack of settings cards of the graphical user interface.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 (e.g., graphical regions, graphical elements, graphical areas, graphical settings cards, graphical stacks or decks of settings cards, graphical animations, parameters, metrics, variables, images, values, limits, text strings, macros, etc.) that may be employed to perform, or carry out, exemplary methods and/or processes (e.g., displaying graphical user interfaces, allowing user interaction with graphical user interfaces, interpreting touch gestures on a touchscreen (e.g., swipes, drags, press-and-hold, touches, presses, etc.), displaying graphical elements, displaying graphs, displaying textual elements, displaying textual values, displaying status information, issuing alarms, running a treatment, determining problems with a treatment, exchanging/changing reservoirs, notifying operators/users of problems, etc.) for use in performing extracorporeal blood treatments. The computing apparatus 12 may be operatively coupled to the input apparatus 20 and the display apparatus 22 to, e.g., transmit data to and from each of the input apparatus 20 and the display apparatus 22. For example, the computing apparatus 12 may be operatively coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical elements, graphical regions, and graphical areas displayed on the display apparatus 22 to, e.g., initiate one or more actions and/or processes related to the extracorporeal blood treatment system, indicate one or more actions and/or statuses related to one or more processes of the extracorporeal blood treatment system, etc.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an operation region containing, or depicting, graphical elements, graphical regions, and graphical areas associated with and representative of (or corresponding to) one or more features or processes of the extracorporeal blood treatment system when used in conjunction with the display apparatus 22 (e.g., displaying the graphical user interface). Further, more specifically, the input apparatus 20 may allow an operator to interact with a graphical user interface including a plurality of settings cards organized and displayed in stacks, or decks, of cards when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more graphical regions, graphical elements, and graphical areas (e.g., settings cards, settings on settings cards, etc.).

For example, the graphical user interface displayed by the display apparatus 22 may include, or display, an operation region that may include multiple graphical regions, graphical areas, and graphical elements related to the extracorporeal blood treatment system. Such graphical regions, graphical areas, and graphical elements may include settings cards configured to allow a user to adjust, or configure, one or more settings associated with one or more processes of the extracorporeal blood treatment system.

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located within a region that is smaller than the region within which the area is located. Still further, as used herein, an "element" of a graphical user interface may be defined as a component of the graphical user interface that may be located within, or adjacent to, a region, an area, or another element. In one or more embodiments, an "element" of a graphical user interface may include a perimeter, or border, defining the outer edge, or boundary, of the element. In one or more embodiments, an "element" of a graphical user interface is a defined, finite portion, item, and/or section of a graphical user interface.

The processing programs or routines 16 may include programs or routines for performing computational mathematics, touchscreen gesture interpretation algorithms, process performance algorithms, process automation algorithms, matrix mathematics, standardization algorithms, comparison algorithms, or any other processing required to implement one or more exemplary methods and/or processes described herein. Data 18 may include, for example, variables, graphics (e.g., graphical elements, graphical areas, graphical regions, settings cards, stacks of settings cards, icons, buttons, windows, dialogs, pull-down menus, 3D graphics, images, animations, etc.), graphical user interfaces, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, or code, e.g., a high level procedural and/or object orientated programming language or code that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., blood circuits, sensors, pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may include systems such as, e.g., dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body via an arterial blood circuit and exposed to a treatment device to separate substances therefrom and/or to add substances thereto, and is then returned to the body via a venous blood circuit. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular treatment system.

Figure 2:
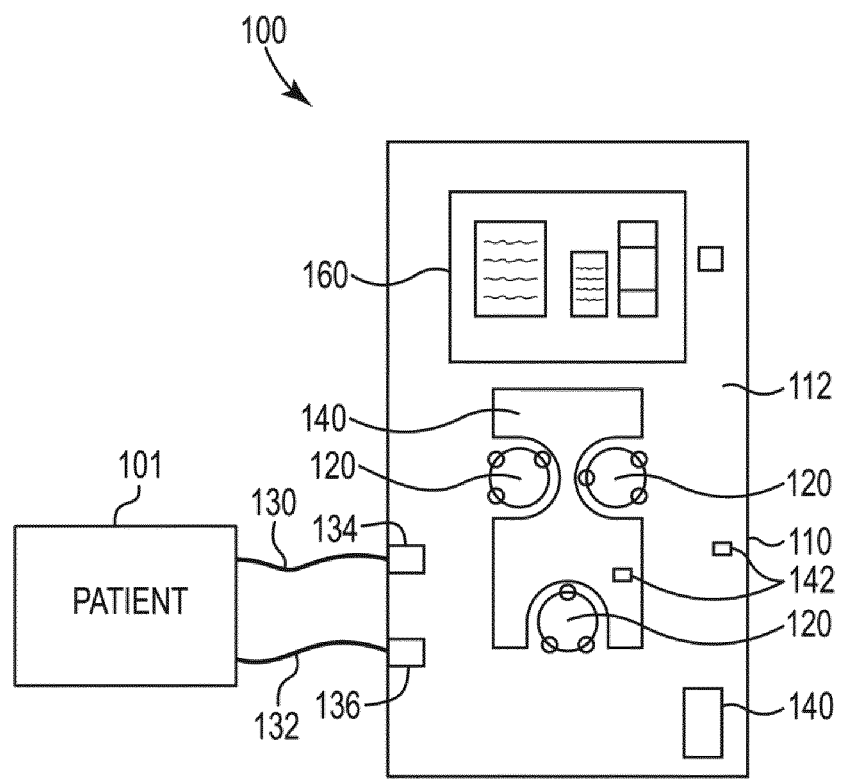
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system 100 further includes one or more pumps 120, one or more disposable elements 140 (e.g., including or part of integrated modules), and one or more sensors 142 for use in performing one or more extracorporeal blood treatments. The one or more pumps 120 may be used to move liquids through the system as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc. and/or may not be visible on the outside of the housing 110. The one or more disposable elements 140 may be coupled to the system 100 for using in performing the extracorporeal blood treatment. The one or more disposable elements 140 may include one or more fluid circuits such as, e.g., dialysis or dialysate fluid circuits, blood circuits, etc. and/or one or more blood treatment units such as, e.g., filters, etc. In at least one embodiment, a disposable element 140 is a cartridge or integrated unit including a plurality of various parts or portions configured to perform the extracorporeal blood treatment. Additionally, the one or more disposable elements 140 may include containers, or vessels, containing, or holding, one or more substances for use in the performance of the extracorporeal blood treatment. For example, a disposable element 140 may include a container, or vessel, holding bicarbonate, citrate, and/or dialysate/dialysis fluid, which may be operatively coupled to the dialysis/dialysate fluid circuit. Further, the disposable elements 140 may be described as providing at least a portion of the extracorporeal blood treatment fluid circuit that may be operatively coupled to one or more pumps 120 and one or more sensors 142 of the system 100 for use in performing extracorporeal blood treatments. As shown, two disposable elements 140 appear to be coupled to the front face 112 of the housing 110 of the system 100 to, e.g., integrate with the one or more other fluid circuits, pumps 120, and sensors 142 of the system 100.

As described herein, the one or more disposable elements 140 may be described as including one or more disposable fluid circuits and one or more blood treatment units operatively coupled to the one or more disposable fluid circuits. The one or more disposable elements 140 may be further described as including a blood circuit for receiving, circulating, and returning blood from/to a patient. The blood circuit may include one or more blood lines (e.g., as part of a disposable element). Further, the one or more disposable elements 140 may be further described as including a dialysis/dialysate circuit operatively coupled, or couplable, to the blood circuit to remove waste from the blood of the patient. The dialysis/dialysate circuit may receive, circulate, and return dialysis/dialysate fluid (e.g., returning dialysis/dialysate fluid including waste). The dialysis/dialysate circuit may include one or more dialysis/dialysate lines (e.g., as part of a disposable element 140). The blood treatment units may be, for example, a plasma filter, a hemodialysis filter, a hemofiltration filter, etc. Generally, the blood treatment units may be referred to as "filters."

As described herein, the system 100 may further include one or more sensors 142. As shown, two sensors 142 are identified on the system 100. One sensor 142 is located on, or coupled to, the front surface 112 of the housing 110 and another sensor 142 is located on the, or coupled to, the disposable elements 140. Additionally, the system 100 may include sensors 142 that are not visible on the outside of the housing 110, and instead, may be internal to the system 100 (e.g., within the housing 110). Generally, the system 100 may include any one or more sensors 142 so as to be able to monitor any value (e.g., any aspect, setting, level, condition, event internal to the system 100, etc.) of any process feature of the system 100 such as, e.g., process features during the performance of one or more extracorporeal blood treatments. For example, the system 100 may include one or more pressure sensors 142 operable to measure, or monitor, various pressures of various circuits, chambers, pods, reservoirs, etc. of the system 100, e.g., during the performance of an extracorporeal blood treatment, during the performance of a pre-treatment process, during the performance of a disinfection, post-treatment process, etc. Further, for example, the system 100 may include one or more flow rate sensors 142 operable to measure, or monitor, various fluid flow rates of fluids within various circuits, chambers, pods, reservoirs, etc. of the system 100, e.g., during the performance of an extracorporeal blood treatment, during the performance of a pre-treatment process, during the performance of a disinfection, post-treatment process, etc. Specifically, the system 100 may include one or more blood-related parameter sensors 142 such as, e.g., flow rate sensors to monitor various blood flow rates throughout the blood circuits of the system 100, blood pressure sensors to monitor the diastolic and systolic blood pressure of the patient, blood circuit pressure sensors to monitor the arterial and venous blood lines pressures, heart rate sensors to measure the patient's heart rate, etc. Further, for example, the system 100 may include one or more waste sensors 142 configured to, or operable, to measure, or monitor, an amount of waste being removing from a patient (e.g., from a patient's blood), e.g., during the performance of an extracorporeal blood treatment. Further, for example the system 100 may include one or more fluid circuit or lines sensors 142 such as, e.g., blood circuit sensors to detect whether a blood circuit is coupled or uncoupled to the system, dialysate/dialysis fluid circuit sensors to detect whether a dialysate/dialysis circuit is coupled or uncoupled to the system, etc. In other words, one or more blood circuit sensors may be configured to detect whether a blood circuit is operatively coupled to the remainder of the extracorporeal blood treatment apparatus for use in an extracorporeal blood treatment and/or one or more dialysate/dialysis fluid circuit sensors may be configured to detect whether a dialysate/dialysis circuit is operatively coupled to the remainder of the extracorporeal blood treatment apparatus for use in an extracorporeal blood treatment. In one or more embodiments, the blood circuit and dialysate/dialysis fluid circuits may include some or all of the same sensors (e.g., when the blood circuit and dialysate/dialysis fluid circuit are part of the same disposable element or cartridge). Still further, for example, the system 100 may include other sensors 142 such as fluid level sensors, temperature sensors, leak detection sensors, etc. that may be used before an extracorporeal blood treatment is performed, during the performance of an extracorporeal blood treatment, and/or after an extracorporeal blood treatment is performed.

Additionally, the extracorporeal blood treatment fluid circuit of the system 100 may be described as being completed by a combination of the disposable elements 140 and the system 100 and may be generally described as defining a blood circuit that removes blood from a patient, for example, via a catheter inserted in a vascular access of the patient, and takes the blood though a blood removal line. Then, the blood may pass through a chamber (e.g., a blood chamber) and, via a return line, may be transported back to the patient.

In one or more embodiments, the extracorporeal blood treatment system 100 may be configured for acute blood treatments (e.g., continuous renal replacement therapy) and may also include one or more devices, apparatus, and structures configured to perform the acute blood treatments. For example, the extracorporeal blood treatment system 100 may include reservoir sensors, or scales, (e.g., weight sensors, load cells, etc.), each of which is configured to hold and weigh a reservoir. The reservoir sensors may be positioned below the bottom end of the housing 110, at least in part because the reservoirs are typically attached to and hang from the reservoir sensors. The extracorporeal blood treatment systems described herein may include one or more reservoir sensors and associated reservoirs such as, e.g., as few as two reservoirs sensors and associated reservoirs, four or more reservoirs sensors and associated reservoirs, etc.

The extracorporeal blood treatment system 100 further includes a venous blood line/circuit 130 extending from a patient 101 (symbolically represented in FIG. 2) to the housing 110 to return blood to the patient 101 after the blood is treated by the system 100, an arterial blood line/circuit 132 extending from the patient 101 to the housing 110 to withdraw blood from the patient 101 for treatment, a venous blood circuit pressure sensor 134 configured to measure, or monitor, the pressure of the venous blood line/circuit 130 (e.g., the pressure of the blood, or fluid, within the venous blood line/circuit 130), and an arterial blood circuit pressure sensor 136 configured to measure, or monitor, the pressure of the arterial blood line/circuit 132 (e.g., the pressure of the blood, or fluid, within the arterial blood line/circuit 132). The venous and arterial blood circuits 130, 132 may connect the patient to a blood circuit (e.g., a disposable element 140) such that, e.g., blood of the patient may be circulated through the blood circuit to perform blood treatments thereon. In other words, the blood circuit may be connectable to a patient using the venous and arterial blood lines 130, 132.

The extracorporeal blood treatment system 100 also includes a display 160 used to show, or convey, information to an operator or user. The display 160 may also serve as an input device if, e.g., the display 160 is in the form of a touchscreen (e.g., a user interactable graphical user interface, etc.). Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to the housing 110 (e.g., a top end of the housing 110).

As shown in FIG. 1 and as related to FIG. 2, the treatment apparatus 24 may be operatively coupled, or connected, to the computing apparatus 12. Among the treatment apparatus 24 operably coupled to the computing apparatus 12 may be the pumps 120, blood circuits/lines 130, 132, blood circuit pressure sensors 134, 136, and disposable elements 140 as shown in FIG. 2.

Exemplary graphical user interfaces, or portions thereof, for use in displaying information related to extracorporeal blood treatments, providing functionality to an operator for use in preparing and performing extracorporeal blood treatments and/or configuring or maintaining an extracorporeal blood treatment system are depicted in FIGS. 4-8. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touchscreen, and in such configuration, the input apparatus would also be the touchscreen.

Each exemplary graphical user interface of the exemplary extracorporeal blood treatment systems and methods described herein may include one or more graphical elements, regions, and areas used to display information to a user. An operator may use input apparatus 20 of the exemplary extracorporeal blood treatment system 10 described herein with reference to FIG. 1 to select or manipulate graphical elements, regions, and areas of the exemplary graphical user interfaces of FIGS. 4-8. As used herein, when an operator "selects" or "interacts with" a graphical element, area, and/or region of the graphical user interface, it is to be understood that "selecting" or "interacting with" the graphical element, area, and/or region to perform one or more tasks or steps may be conducted in many different ways using many different types of input apparatus. For example, when the input apparatus includes a touch screen, an operator may select or interact with a graphical element, area, and/or region by "touching" the graphical region with their finger or using a pointing device such as a stylus. Further, for example, when the input apparatus includes a mouse or similar pointing device, an operator may select or interact with a graphical element, area, and/or region by locating an arrow or cursor over the desired graphical region "clicking" the graphical region. Still further, for example, when the input apparatus includes a series of buttons and/or knobs, an operator may select or interact with a graphical element, area, and/or region by using the buttons and/or knobs to navigate to the graphical region and to select it (e.g., by depressing the button and/or knob). Additionally, it is to be understood that selection of or interaction with a graphical element, area, and/or region may be conducted using various gestures such as, for example, but not limited to, swipes, select-and-drag, press, tracing of various shapes, pinch-inwardly, pinch-outwardly, finger spread, multi-finger touches and/or swipes, etc.

Figure 3:
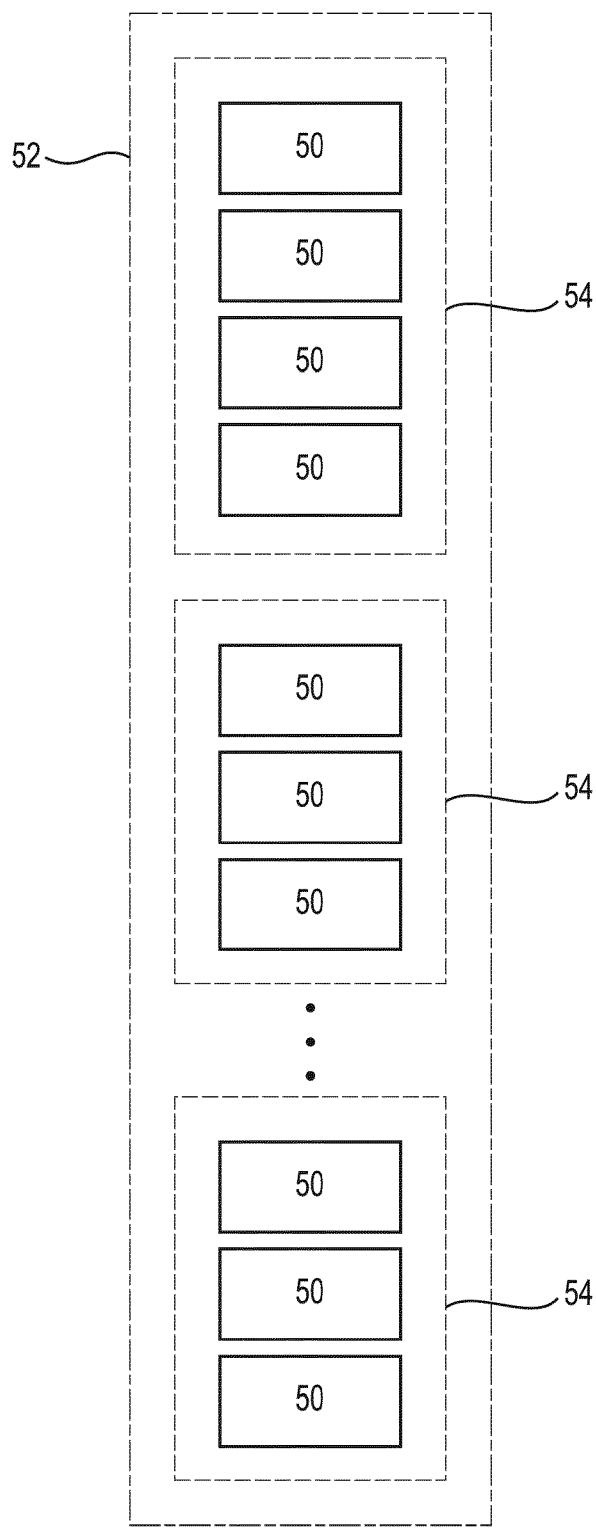
FIG. 3 is a diagrammatic illustration of a plurality of grouped settings cards for use on an exemplary graphical user interface of the extracorporeal blood treatment system such as, for example, shown generally in FIGS. 1-2.

The exemplary systems and methods may include providing, or using, a plurality of settings cards 50, which are diagrammatically illustrated in FIG. 3. Each of the settings cards 50 may be configured to be displayed on an exemplary graphical user interface of an extracorporeal blood treatment system such as, for example, shown generally in FIGS. 1-2, and each of the settings cards 50 may be configured to display one or more settings related to one or more processes of the extracorporeal blood treatment system as will be shown further herein with respect to FIGS. 4-8.

The plurality of settings cards 50 may be grouped, or placed, into one or more card sets or card subsets as shown in FIG. 3. For example, all of the settings cards 50 may be grouped into a master, or complete, card set 52 outlined by a broken line. Further, some of the settings cards 50 may be grouped into smaller groups than the card set 52 such as card subsets 54, which are also outlined by broken lines. In other words, all settings cards 50 may be selected, or configured, to be part of the card set 52, and less settings cards 50 than the card set 52 may be selected, or configured, into card subsets 54. Further, although it is not shown, it is to be understood that some card subsets 54 may include settings cards 50 that are also part of other card subsets 54. In other words, some card subsets 54 may "overlap" with other card subsets 54.

The master, or complete, card set 52 may be associated with, or for, an exemplary treatment cycle. In other words, all of the settings cards 50 may be defined as each and every settings card 50 that includes settings and/or parameters related to the present treatment cycle including preparation, treatment, and post-treatment portions. Further, it may be described that all of the settings cards 50 of set 52 may not include cards that are not associated with the treatment cycle such as, e.g., service and maintenance cards, system preference cards, and/or a calculator card.

Figure 4:
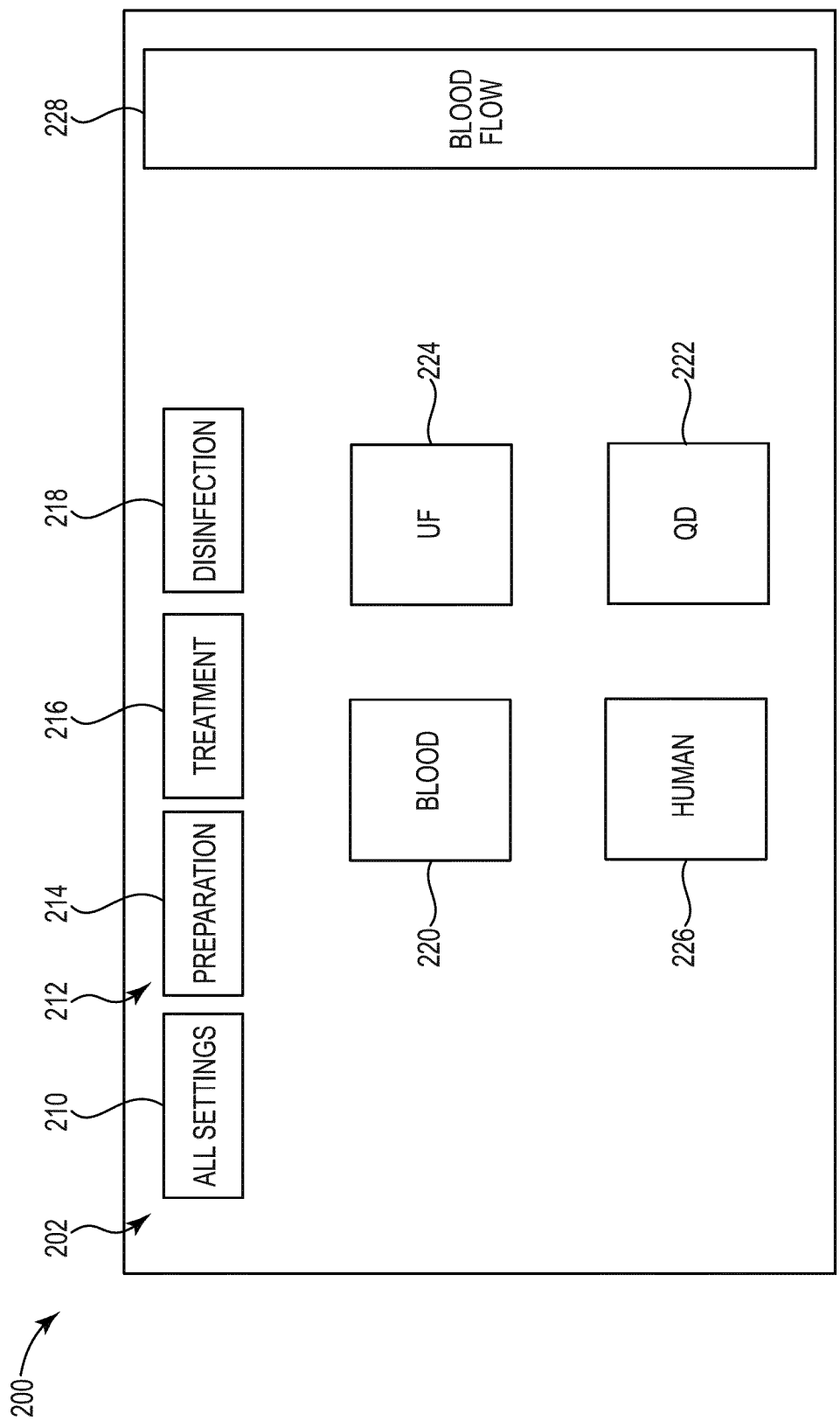
FIG. 4 depicts an exemplary graphical user interface for use on an extracorporeal blood treatment system such as, for example, shown generally in FIGS. 1-2.

An exemplary graphical user interface 200 is depicted in FIG. 4 that may be generally used to perform one or more processes provided by an extracorporeal blood treatment system. As shown, the graphical user interface 200 may include a plurality of graphical regions, graphical areas, and graphical elements 202 that may be used in the preparation or performance of an extracorporeal blood treatment as well as other functionality and/or processes of the extracorporeal blood treatment system. For example the graphical regions, graphical areas, and graphical elements 202 may be used to indicate, initiate, revert, and stop one or more process features of one or more processes of the extracorporeal blood treatment system. In the exemplary graphical user interface 200, some of the graphical regions, graphical areas, and graphical elements 202 may correspond to (e.g., representative of, associated with, etc.) a card set 52 and/or one or more card subsets 54 described herein with respect to FIG. 3.

For example, the plurality of graphical regions, graphical areas, and graphical elements 202 may include an all-settings graphical element 210 corresponding to a set of all of a plurality of exemplary settings cards and a plurality of card subset graphical elements 212, each corresponding to a subset of the plurality of exemplary settings cards. In particular, the card subset graphical elements 212 include a "Preparation" card subset graphical element 214, a "Treatment" card subset graphical element 216, and a "Disinfection" card subset graphical element 218. Each of the card subset graphical elements 212 depicted may be associated with a different chronological phase, or portion, of a process performed by the extracorporeal blood treatment system, and further may be arranged, or depicted, on the graphical user interface 200 in such chronological order. In this example, the "Preparation" card subset graphical element 214, the "Treatment" card subset graphical element 216, and the "Disinfection" card subset graphical element 218 may be associated with the preparation, execution, and post-treatment procedures and processes of an extracorporeal blood treatment such as, e.g., a dialysis treatment.

Figure 5A:
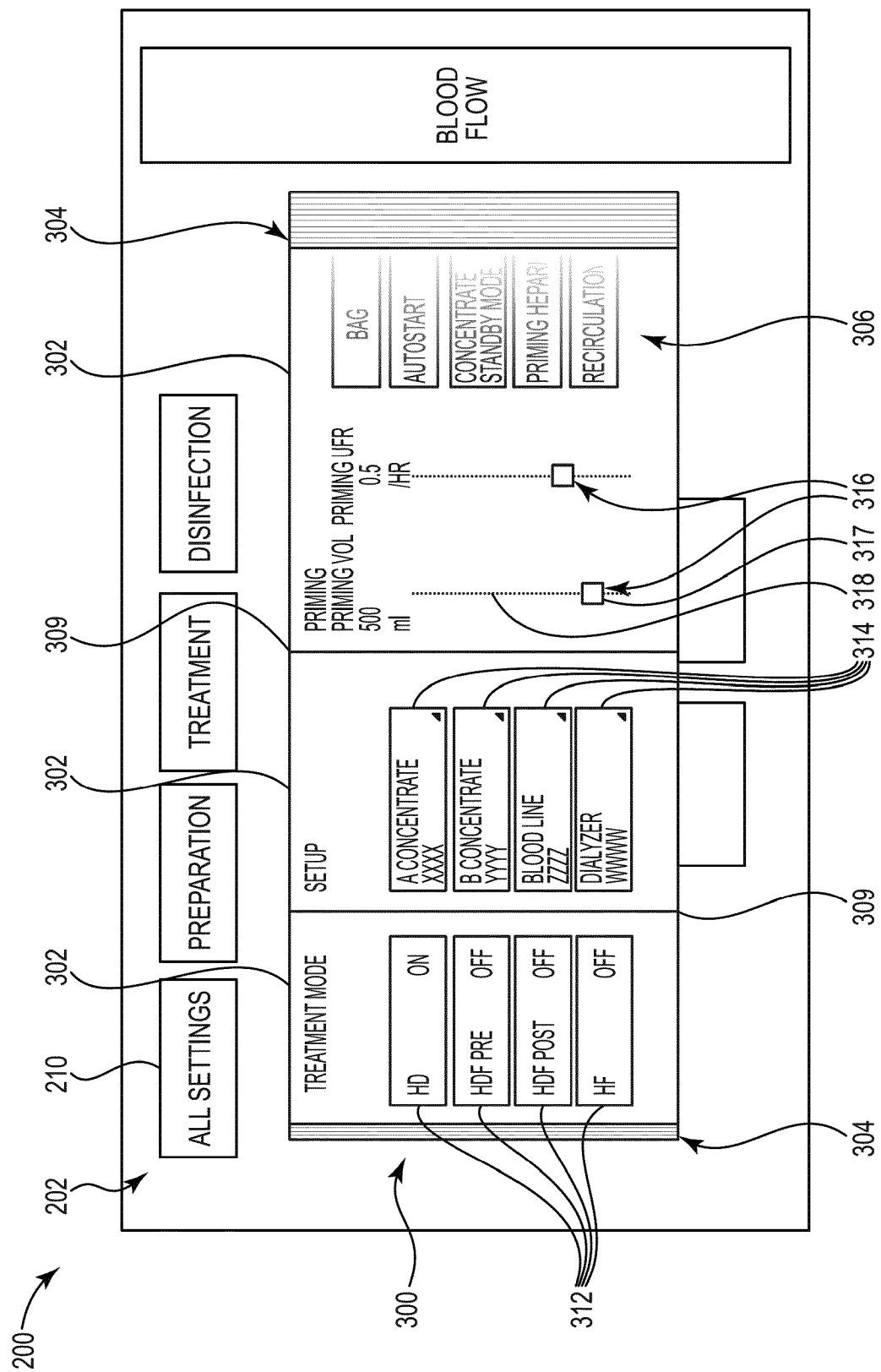
FIGS. 5A-5B depict the graphical user interface of FIG. 4 including an exemplary stack of a settings card set.
Figure 5B:
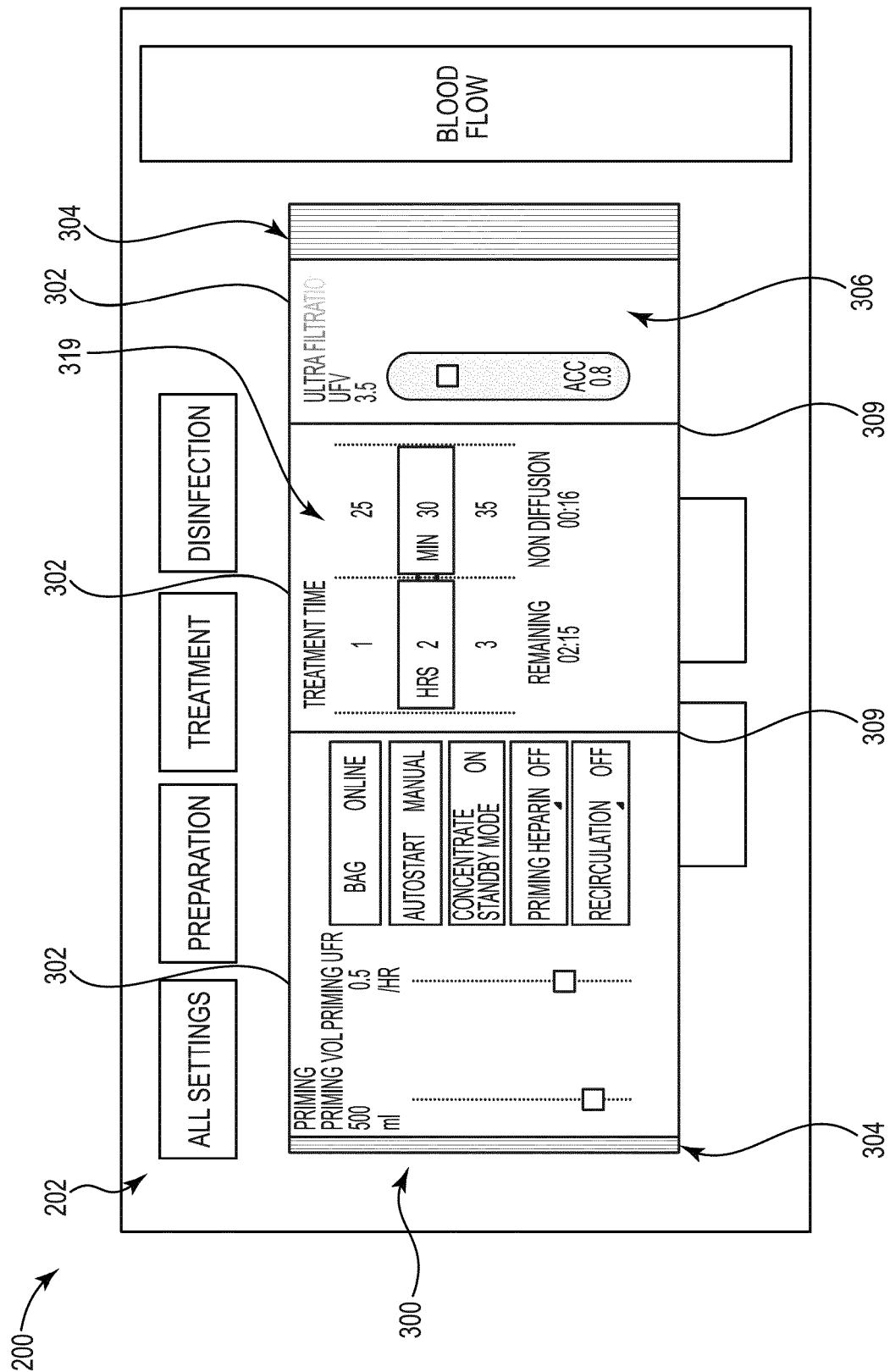
Figure 6A:
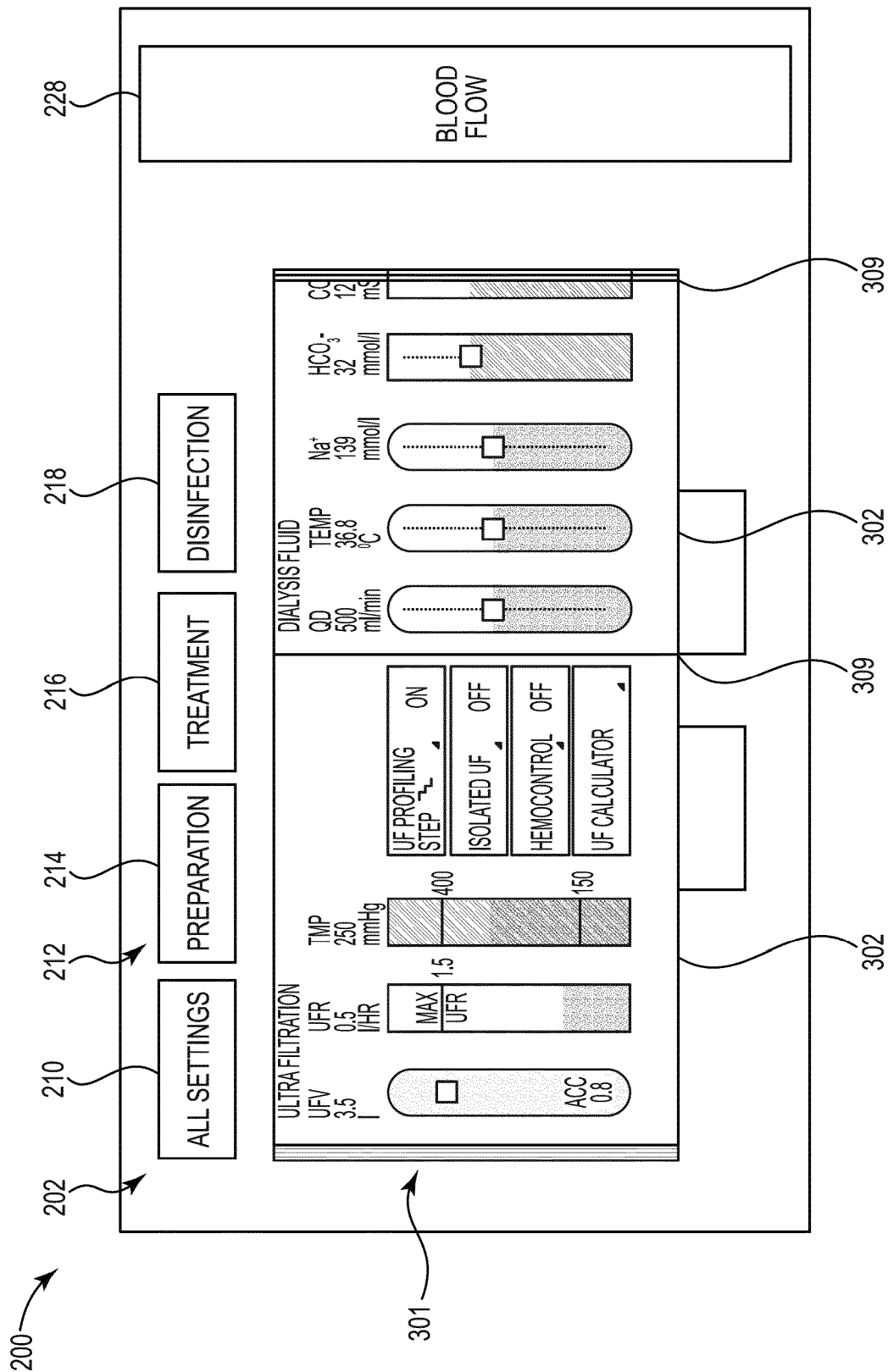
FIGS. 6A-6C depict the graphical user interface of FIG. 4 including an exemplary stack of a settings card subset.
Figure 6B:
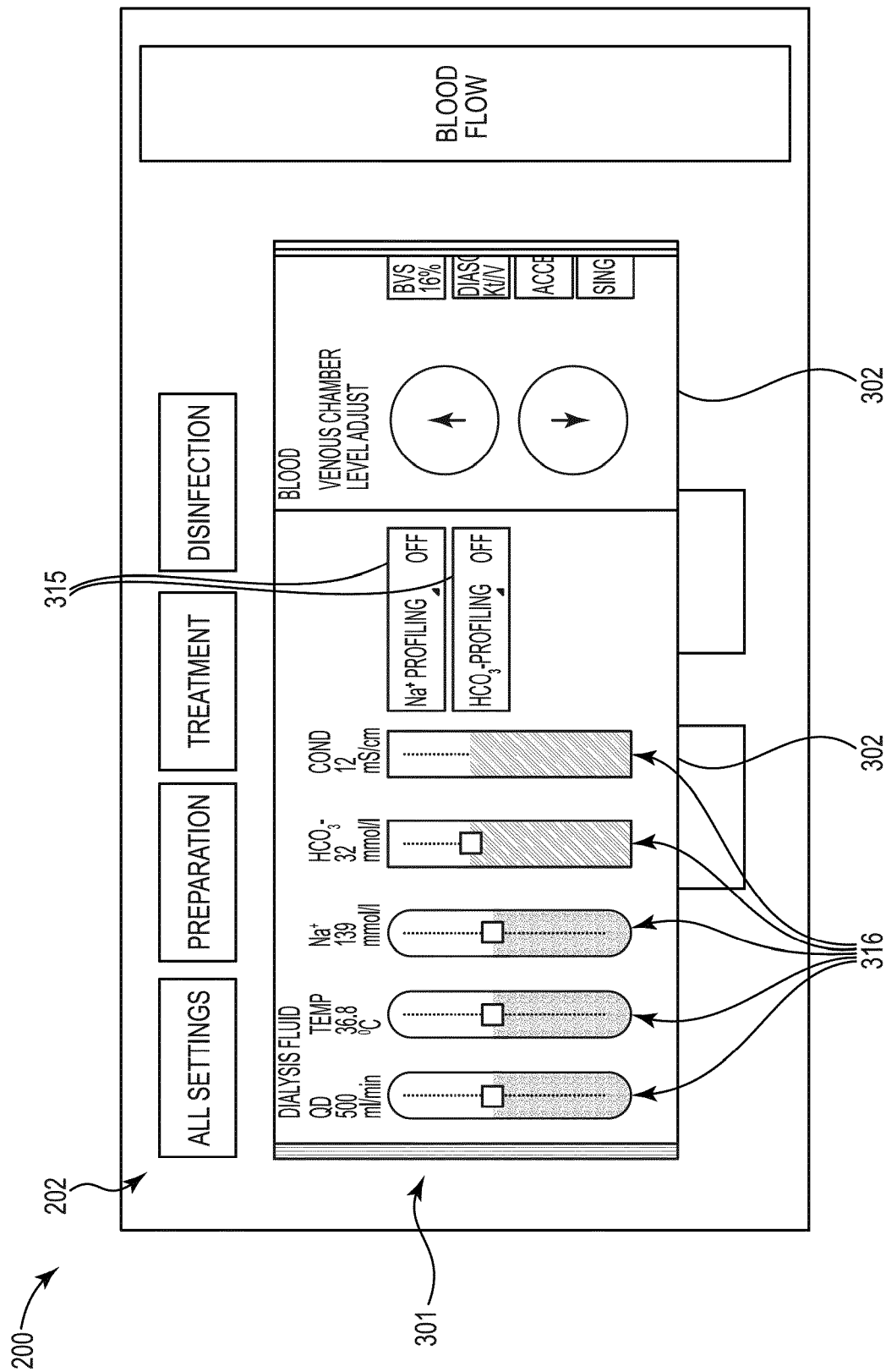

The selection of one of the all-settings graphical element 210 and the plurality of card subset graphical elements 212 may display the card set or card subset of settings cards associated therein. For example, selection of the all-settings graphical element 210 may display a stack 300 of a set (e.g., master set) of exemplary settings cards (e.g., all settings cards) as shown in FIGS. 5A-5B. Further, for example, selection of one of the card subset graphical elements 212 may display a stack 301 of a card subset of exemplary settings cards 302 as shown in FIGS. 6A-6B. More specifically, the "Preparation" card subset graphical element 214 may be selected to display a stack of a card subset of settings cards 302 related to the "Preparation" phase of a blood treatment, the "Treatment" card subset graphical element 216 may be selected to display a stack of a card subset of settings cards 302 related to the "Treatment" phase of a blood treatment, and the "Disinfection" card subset graphical element 218 may be selected to display a stack of a card subset of settings cards 302 related to the "Disinfection" phase of a blood treatment.

Figure 7A:
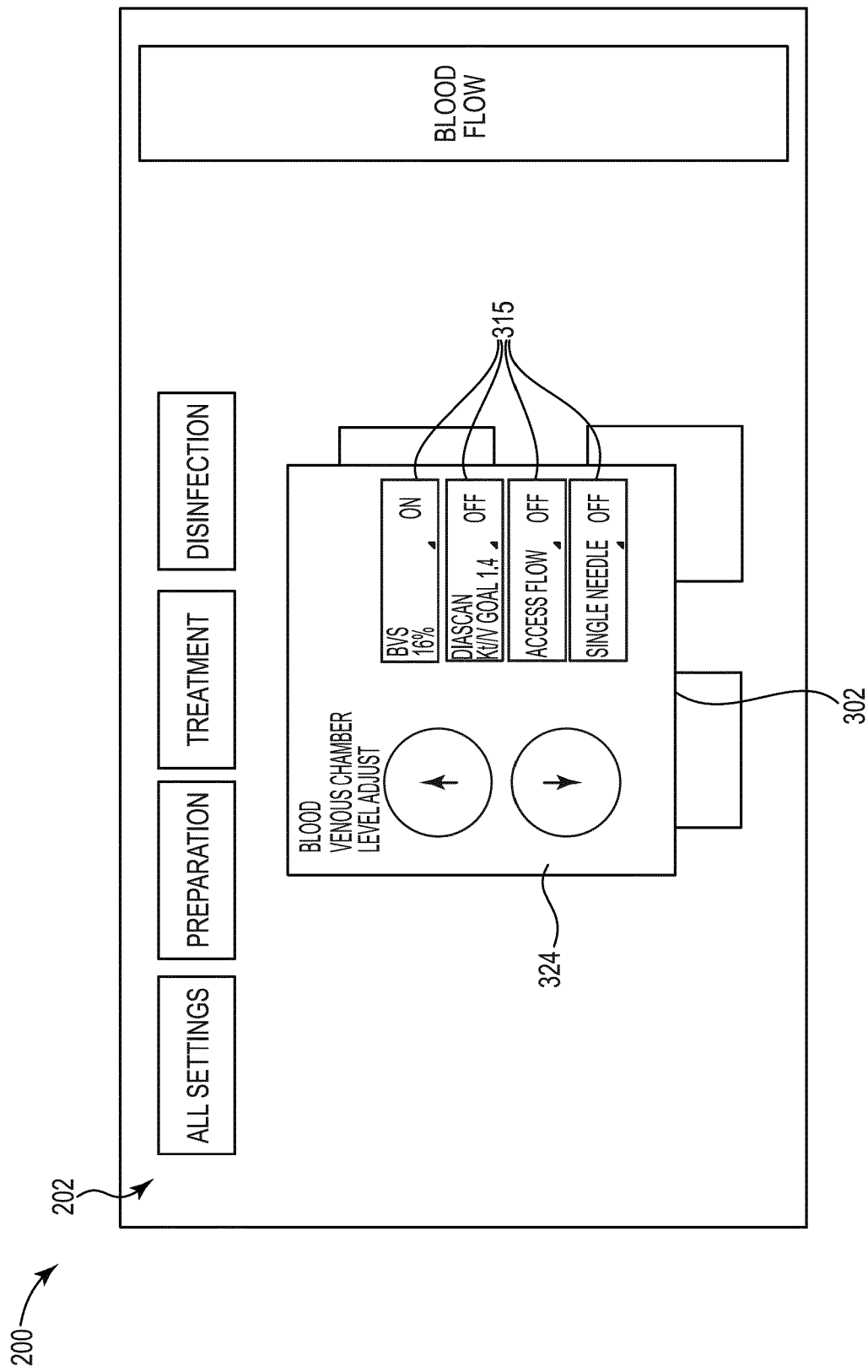
FIG. 7A depicts the graphical user interface of FIG. 4 including an exemplary single "Blood" settings card.

Further, in the exemplary graphical user interface 200, some of the graphical regions, graphical areas, and graphical elements 202 may correspond to (e.g., representative of, associated with, etc.) to single process features of the one or more processes performable by the extracorporeal blood treatment system. For example, at least some of the graphical regions 202 related to an on-going extracorporeal blood treatment may include a blood process feature graphical element 220, dialysis fluid process feature graphical element 222, an ultrafiltration process feature graphical element 224, a human process feature graphical element 226, and a blood flow process feature graphical element 228. Additionally, when a blood treatment is not being performed, such as during setup before a blood treatment is performed or during disinfection after a blood treatment is performed, the graphical elements 220, 224, 226, 228 may not be directly-related to a blood treatment but instead may be related to the setup (e.g., entering of a prescription) or disinfection. Selection of the blood process feature graphical element 220, dialysis fluid process feature graphical element 222, an ultrafiltration process feature graphical element 224, a human process feature graphical element 226, and a blood flow process feature graphical element 228 may display a single settings card 302 related to the selected graphical element as will be described herein with respect to FIG. 7A. More specifically, selection of the blood process feature graphical element 220 may display the single "Blood" settings card 324 as shown in FIG. 7A.

In response to selection of the all-settings graphical element 210, a stack 300 of the set (e.g., master set) of the settings cards 302 is displayed, or depicted, on the graphical user interface 200 as shown in FIG. 5A. The stack 300 of settings cards 302 may be described as a graphical depiction of a three-dimensional stack, or pile, of physical cards, or tiles, with one or settings cards 302 located at the forefront, or "on top," of the stack 300 such that these settings cards 302 are presented to the user (e.g., the user may see and modify the settings located in the settings cards 302). The stack 300 of settings cards 302 may include edges 304 of the settings cards 302 located behind the forefront or "topmost" settings cards 302 to, e.g., indicate that more than the presented, forefront settings cards 302 are located in the stack 300 behind the presented, forefront settings cards 302. As described, the stack 300 of the settings cards 302 may be a set of settings cards 302 that includes all of the settings cards 302 as provided by the exemplary system (in other words, the stack 300 may include the master set of settings cards 302). In at least one embodiment, all of the settings cards 302 may be defined as each and every settings cards 302 as provided by the exemplary system for an exemplary treatment cycle. For example, all of the settings cards 302 may be defined as each and every settings card 302 that includes settings and/or parameters related to the present treatment cycle including preparation, treatment, and post-treatment portions. Further, it may be described that all of the settings cards 302 may not include cards that are not associated with the treatment cycle such as, e.g., service and maintenance cards, system preference cards, and/or a calculator card. In at least one embodiment, all of the settings cards 302 may be defined as a selected group of settings cards 302 selected by an administrator to be largest group of settings cards 302 presentably to user by the exemplary system.

As shown, more than one settings card 302 may be displayed, or presented, to the user at the same time as determined by the size of the displayed, or topmost, settings cards 302. In this example, the "Treatment Mode" settings card 302 and "Setup" settings card 302 are displayed or presented while only the edges 304 of the remaining settings cards 302 of the stack 300 are depicted on the graphical user interface 200. Further, a card delineation graphical element 309 may be provided, or depicted, between different settings cards 302 to, e.g., show that the settings cards 302 are separate from each other. In this example, the card delineation graphical element 309 is a line.

Only a portion of the "Priming" settings card 302 is displayed because, e.g., the entire "Priming" settings card 302 may not fit on the graphical user interface 200 or within the allotted spaced for the settings cards 302 on the graphical user interface 200. A region 306 of the "Priming" settings card 302 proximate (e.g., near, next to, etc.) the edges 304 of the stack 300 may include, or depict, a graphical indication that the entire "Priming" settings card 302 is not displayed. In this example, the region 306 is grayed-out from left to right as shown so as to appear to disappear into the edges 304 of the stack 300. In other embodiments, different graphical indications may be provided to indicate that an entire settings card 302 is not shown or displayed. Although two full settings cards 302 and a portion of another settings card 302 are shown, or topmost, in the stack 300, it is to be understood that the exemplary systems and methods may be configured to only display a single settings card 302 at a time from the stack or only display a selected number of settings cards 302 (e.g., two or more settings cards 302, four or more settings cards 302, three or less settings cards 302, five or less settings cards 302, etc.) at a time from the stack 300.

Additionally, the amount, or number, of edges 304 depicted may indicate how many cards are "stacked" behind each side of the stack 300 of settings cards 302. In this example, fewer edges 304 are depicted on the left side of the stack 300 than the edges 304 depicted on the right side of the stack 300 thereby indicating that fewer settings cards 302 are located to the left of the topmost, displayed settings cards 302 than are located to the right of the topmost, displayed settings cards 302. Since the edges 304 may be depicted on either side of the stack 300, it is to be understood that the stack 300 of settings cards 302 may not be thought of as a single physical stack of cards but rather a carousel of cards that may be rotated (e.g., swiped, etc.) to display the settings cards 302 that are located to the left or right of the currently-displayed, topmost settings cards 302.

Each of the settings cards 302 may include one or more settings 310 related to one or more process features of the exemplary extracorporeal blood treatment systems. The one or more settings 310 may often be more than one setting, and thus, be described as a plurality of settings. The settings 310 may include a plurality of different types of settings elements such as, e.g., on/off switch elements 312, item selection elements 314, and bar-type parameter adjustment elements 316 as shown in FIG. 5A. The switch elements 312 may be configured to allow a user to select whether a particular process feature is "on" or "off" (e.g., "true" or "untrue," "used" or "unused," etc.). As shown, the switch elements 312 in the "Treatment Mode" settings card 302 indicate that hemodialysis (HD) treatment is "on," hemodiafiltration pre-dilution (HDF Pre) treatment is "off," hemodiafiltration post-dilution (HDF Post) treatment is "off," and hemofiltration (HF) treatment is "off." In other words, the exemplary system may provide hemodialysis treatment, hemodiafiltration pre-dilution treatment, hemodiafiltration post-dilution treatment, and hemofiltration treatment, and the user has selected the hemodialysis treatment switch element 312 to perform hemodialysis treatment.

The item selection elements 314 may be configured to allow a user to select an item from a list, or group, of items. As shown, the item selection elements 314 of the "Setup" settings card 302 indicate that a user has selected "XXXX" for the "A Concentrate," "YYYY" for the "B Concentrate," "ZZZZ" for the "Blood Line," and "WWWW" for the "Dialyzer." Upon selection (e.g. touch, tap, click, etc.) of a selection element 314, a list, or group, of the selectable items may be displayed, which may then be selected by the user.

The bar-type parameter adjustment elements 316 may be used to adjust a numerical parameter of a process feature using a handle element 317 movable along a bar element 318. As shown, the "Priming Volume" is currently 500 milliliters (ml) and the "Priming Ultrafiltration Rate" is 0.5 liters per hour, and a user may use the bar-type parameter adjustment elements 316 to adjust each of these values. For example, as user may select the handle element 317 and move the handle element 317 upwardly or downwardly along the bar element 318 to adjust the numerical parameters associated therewith.

If a user would like to see more of the "Priming" settings card 302 and/or other settings cards 302 within the stack 300 of settings cards 302, a user may perform a deliberate action to move un-displayed settings cards 302 to the top of the stack 302 such that the un-displayed settings cards 302 will be displayed. For example, a user may perform a swiping gesture on the stack 300 in FIG. 5A from right-to-left (e.g., towards the left set of edges 304) to move the topmost, displayed settings cards 302 to the left set of edges 304 thereby hiding those settings cards 302 (e.g., "stacking" such settings cards 302) while simultaneously pulling hidden, or un-displayed, settings cards 302 from the right set of edges 304 to the topmost position and thereby displayable. More specifically, as shown in FIG. 5B, the entire "Priming" settings card 302, a "Treatment Time" settings card 302, and a portion of an "Ultrafiltration" settings card 302 have now been moved to be topmost in the stack 300 and displayable while the "Treatment Mode" settings card 302 and "Setup" settings card 302 have been moved back into the stack 302 and not displayed. As now shown, the "Priming" settings card 302 further depicts a plurality of the switch elements 312 in addition to the bar-type parameter adjustment elements 316.

The "Treatment Time" settings card 302 includes a time selection graphical element 319 configured to allow a user to select the treatment time for the selected blood treatment. More specifically, the time selection graphical element 319 may allow users to swipe "up" or "down" along an hour wheel and a minutes wheel to select the desired treatment time.

As described herein, the settings cards 302 may be grouped into card subsets smaller than the set of all settings cards 302, which was displayed in response to selection of the all-settings graphical element 210. The card subsets may be displayed by selecting one of the plurality of card subset graphical elements 212, each of which corresponds to a card subset. For example, upon selection of the "Treatment" card subset graphical element 216, a card subset of settings cards 302 related to the treatment phase of a blood treatment may be displayed in a stack 301 of settings cards 302 as shown in FIGS. 6A-6B.

As shown, the stack 301 of settings cards 302 includes less settings cards 302 than the stack 300 of the set of all settings cards 302 depicted in FIGS. 5A-5B, which, for example, may be indicated by less edges 304 depicted on either side of the stack 301. In the stack 301 in FIG. 6A, the "Ultrafiltration" settings card 302 and a portion of the "Dialysis Fluid" settings card 302 are topmost and displayable. Similar to the stack 300 of FIGS. 5A-5B, an action such as, e.g., a swipe, etc., may be performed proximate the stack 301 to change which settings cards 302 are topmost and displayable (e.g., presentable to a user such that a user can view and/or adjust the one or more settings). As shown in FIG. 6B, the stack 301 has been swiped from right to left to display the entire "Dialysis Fluid" settings card 302 and at least a portion of the "Blood" settings card 302.

Figure 6C:
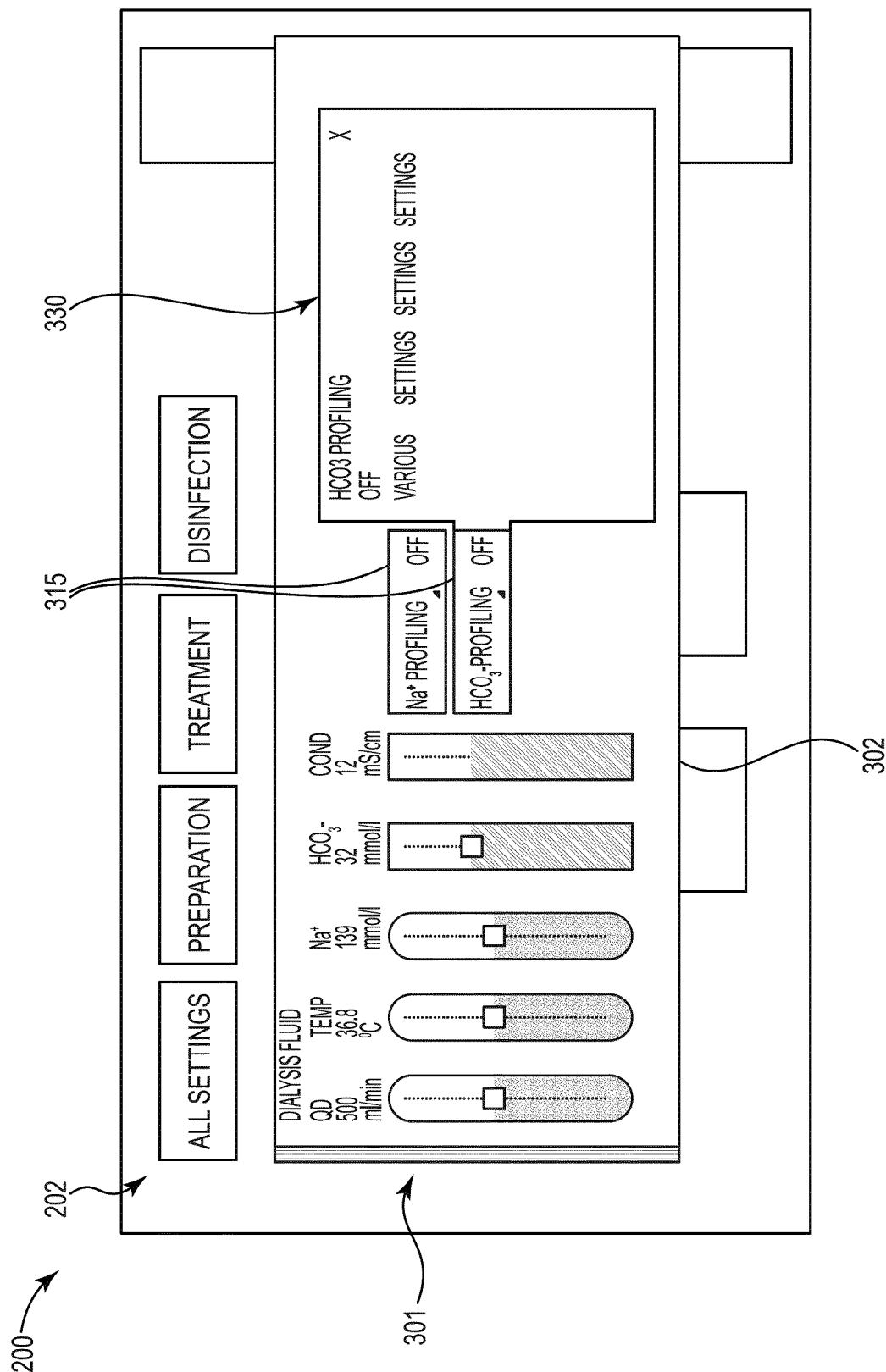

In addition to the bar-type parameter adjustment elements 316, the "Dialysis Fluid" settings card 302 may further include hybrid on/off switch and item selection elements 315 that, upon selection, may display an expanded card area 330 as shown in FIG. 6C. More specifically, a user has selected the "$HCO_{3-}$ Profiling" hybrid on/off switch and item selection element 315 to display a "$HCO_{3-}$ Profiling" expanded card area 330 that displays one or more various settings related to "$HCO_{3-}$ Profiling." As shown, the $HCO_{3-}$ Profiling is not activated yet and is presently turned "off." Upon activation (e.g., by selection of the word "off" in the "$HCO_{3-}$ Profiling" expanded card area 330), one or more settings and parameters related to "$HCO_{3-}$ Profiling" may be modifiable and/or configurable using the expanded card area 330. For example, one or more item on/off switch elements 312, selection elements 314, bar-type parameter adjustment element 316, and/or any other parameter and/or settings-related graphical elements may be displayed in the expanded card area 330 and may be used by a user to modify or configure such settings and/or parameters.

Each of the settings cards 302 may correspond to (e.g., be associated with, relate to, etc.) an individual graphical region, graphical area, or graphical element 202 of the graphical user interface 200 that, upon selection thereof, will display the settings cards 302 corresponding thereto. For example, as shown in FIG. 7A, the "Blood" settings card 302 may be displayed by itself on the graphical user interface 200 upon selection of the "Blood" process feature graphical element 220 of the graphical user interface 200 of FIG. 4. The "Blood" settings card 302 may include a "Level Adjust" graphical element 324 for adjusting the venous chamber blood level and a plurality of hybrid on/off switch and item selection elements 315 for adjusting and/or configuring (BVS), Diascan, Access Flow, and Single Needle.

Thus, each settings card 302 may be described as being accessible by a user through a plurality of different actions or processes. For example, a user may select an all-settings graphical element 210 to display a stack 300 of a set of all of the settings cards 302, a user may select one of the card subset graphical elements 212 to display a stack of a card subset of settings cards 302 corresponding to the selected card subset graphical element 212, or a user may select a process feature graphical element depicted on the graphical user interface 202 (e.g., such as "Blood" process feature graphical element 220 as shown in FIG. 7A) to display a single settings card 302 corresponding to the selected process feature graphical element 202.

Further, one or more settings cards 302 (e.g., a stack of settings cards 302 including a card set or a card subset of settings cards 302, a single settings card 302, etc.) may be displayed, or depicted, on the graphical user interface 200 in response to one or more events of the extracorporeal blood treatment system (e.g., events that are not directly initiated by a user). One or more events, which trigger, or initiate, the display of one or more settings cards 302, may include one or more alarms, one or more timers (e.g., expiration of treatment time, etc.), and/or one or more user-performed tasks. For example, a single settings card 302 may be displayed automatically in response to, or based on, the occurrence of one or more events as shown herein with respect to FIG. 7B.

Figure 7B:
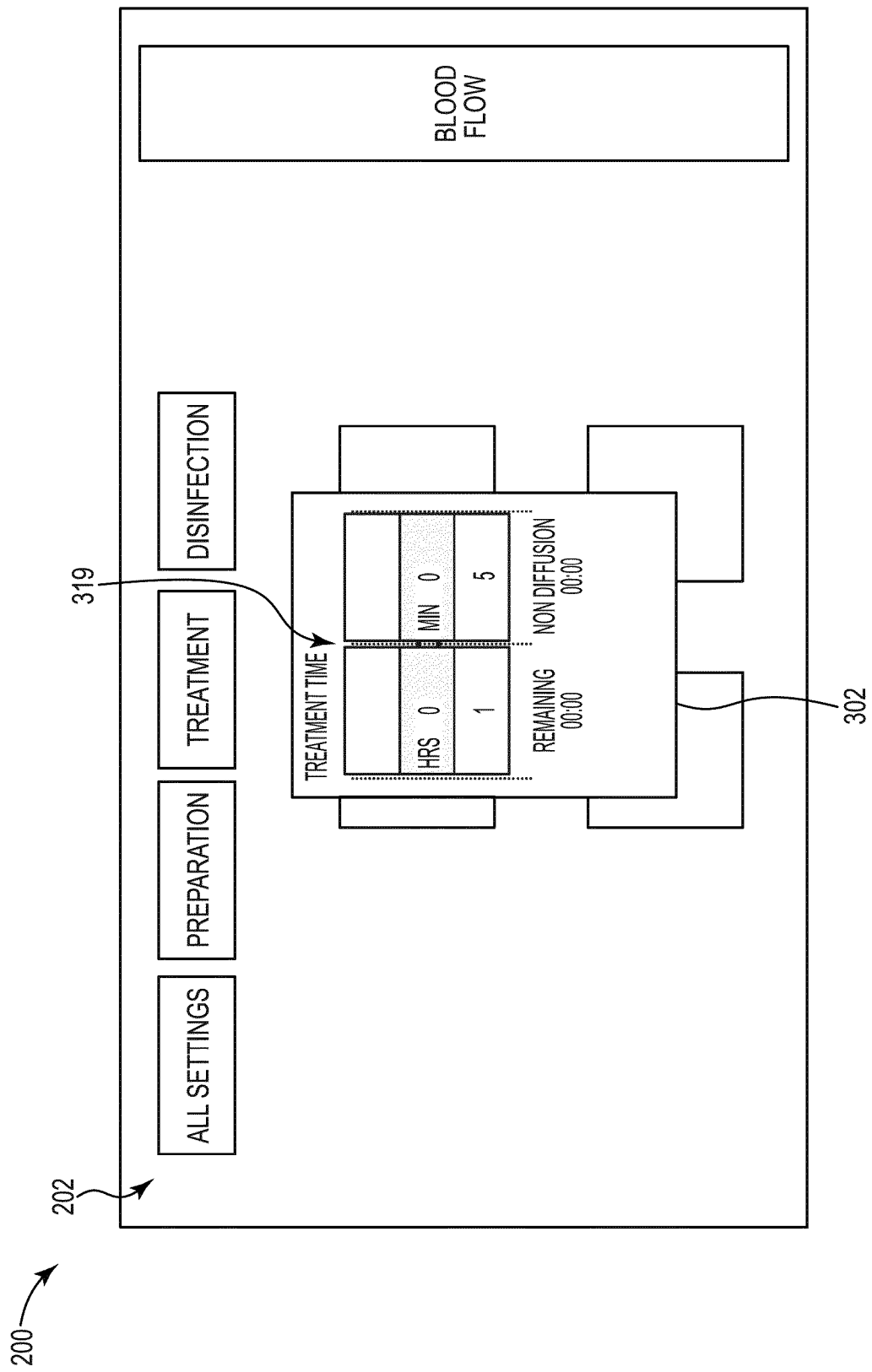
FIG. 7B depicts the graphical user interface of FIG. 4 including an exemplary single "Treatment Time" settings card.

More specifically, as shown in FIG. 7B, the "Treatment Time" settings card 302 may be displayed by itself on the graphical user interface 200 in response to expiration of the treatment time such that, e.g., a user may use the "Treatment Time" settings card 302 to add time to the present treatment if desired. As shown, the remaining treatment time is "00:00," and a user may use the time selection graphical element 319 to add treatment time to the blood treatment.

Further, for example, the stack 301 of the card subset of settings cards 302 related to "Treatment" may be displayed in response to the preparation, or setup, phase of treatment being completed. Still further, for example, a stack of a card subset of settings cards 302 related to "Disinfection" may be displayed in response to the treatment phase of the blood treatment being completed (e.g., the patient is disconnected, etc.). In other words, one or more settings cards 302 may displayed, or depicted, on the graphical user interface 200 automatically based on, or in response to, one or more events occurring to or by the extracorporeal blood treatment system, and the one or more events may correspond to timers, phases of treatment, and/or actions taken by a user.

The exemplary systems and methods may be further configured to allow users such as, e.g., system administrators, clinic directors, etc. to customize the card sets and card subsets. For example, these particular users may be allowed to select, or customize, the order of the plurality of settings cards for each card set or card subset. Further, for example, users may be allowed to select, or customize, which settings cards belong in, or are displayed within, each card set or card subset.

Figure 8:
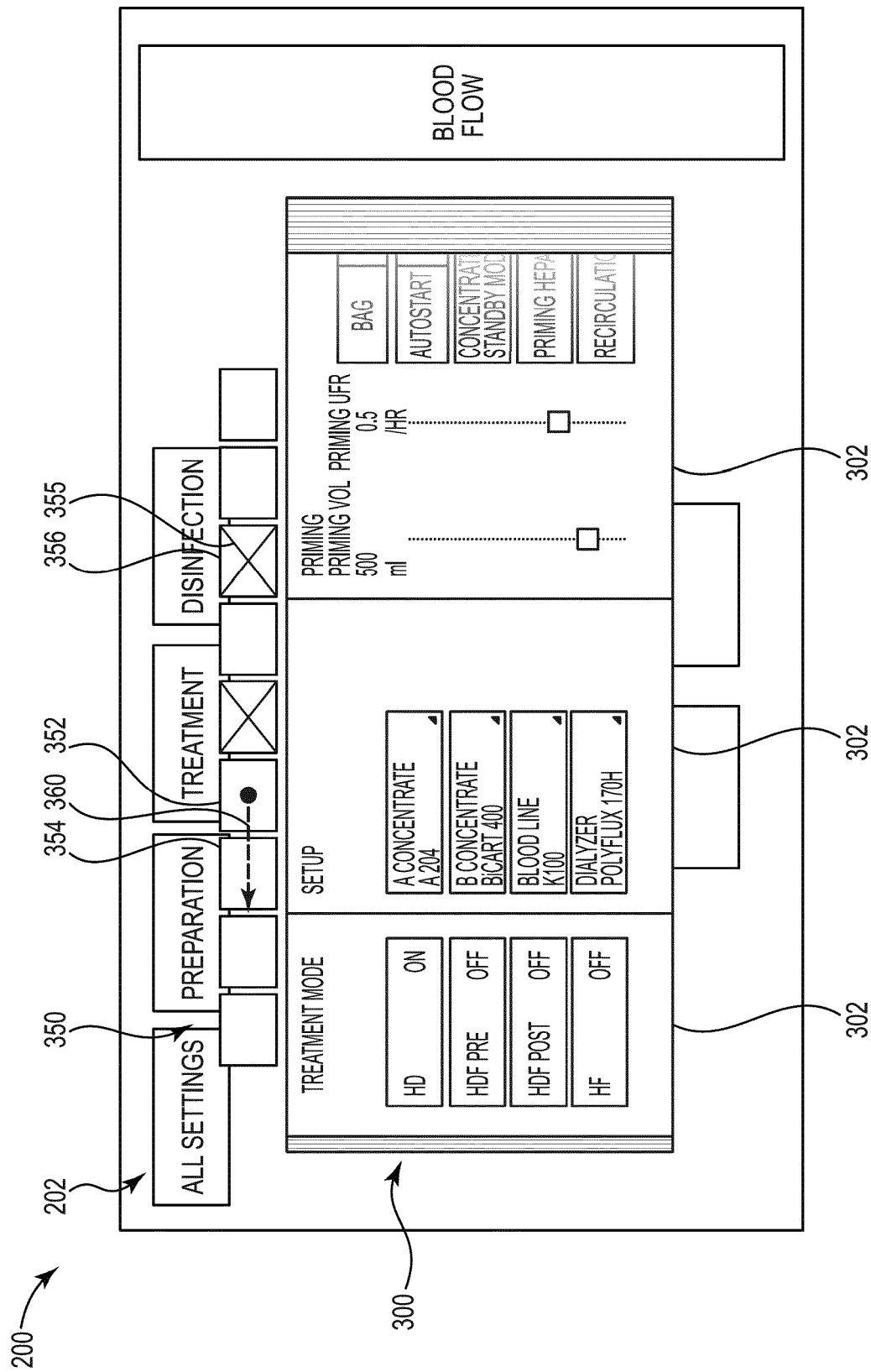
FIG. 8 depicts the graphical user interface of FIG. 4 including an exemplary stack of the settings cards set and settings cards selection and arrangement functionality.

Exemplary settings cards selection and arrangement functionality is depicted on the graphical user interface 200 in FIG. 8. As shown, a plurality of settings card representations 350 (e.g., icons, graphics, symbols, miniaturized versions, etc.) may be depicted proximate (e.g., above) the stack 300 of settings cards 302. Although, in this example, the card set of all settings cards 302 stack 300 is depicted, it is to be understood that the same interface and operations may be performed with each card subset of settings cards 302 such as the "Treatment" stack 301 described herein with respect to FIGS. 6A-6B.

Each of the settings card representations 350 may represent, correspond to, or be associated with, one settings card 302 of the plurality of settings cards 302 and may be used to control, or customize, the order of each settings card 302 with the presently-displayed stack 300 and to control, or customize, whether each settings card 302 is to be displayed in the presently-displayed stack 300.

For example, as shown, a user may select (e.g., touch) and move (e.g., drag without releasing contact with a touchscreen) a settings card representation 350 to another location along the plurality of settings card representations 350 as represented by arrow 360 to move the settings cards 302 associated thereto to a new location within the stack 300. As shown, the settings card representation 352, which may correspond to the "Setup" settings card 302, is being moved to the left of the settings card representation 354, which corresponds to the "Treatment Mode" settings card 302 thereby moving the "Setup" settings card 302 to the left of the "Treatment Mode" settings card 302 within the stack 300. Thus, the order of the settings cards 302 with the stack 300 may be changed by moving settings card representations 350 among the plurality of settings cards representations 350. In other words, the order of the settings card representations 350 may dictate, or configure, the order of the settings cards 302 within the stack 300.

All of the settings cards 302 available to be used with the exemplary systems and methods may be represented on the graphical user interface 200 by the settings card representations 350 when, e.g., an administrator is customizing the card sets and subsets. The settings cards 302 that are not displayed in the presently-displayed stack 300 may be indicated by a not-shown indication 355 proximate the settings card representations 350 corresponding thereto. For example, as shown, an "X," which is the not-shown indication 355 in this embodiment, is depicted over, or on, the settings card representation 356 thereby indicating that the settings card 302 corresponding to the settings card representation 356 is not included in the present card set, and thus, not displayed in the presently-displayed stack 300.

Users may be able to select which settings cards 302 are displayed in the presently-displayed stack 300. For example, a user may select (e.g., touch) and maintain selection (e.g., drag without releasing contact with a touchscreen) a settings card representation 350 to customize whether the corresponding settings card 302 should be displayed in the presently-displayed stack 300 of settings cards 302. For example, a user may select and maintain selection of a settings card representation 350 that does not include a not-shown indication 355 ("X") depicted thereon to remove the corresponding settings card 302 from the card set and stack 300. Afterwards, the not-shown indication 355 will be depicted in the settings card representation 350 to indicate that the settings card 302 corresponding thereto has been removed from the card set and stack 300. To add a settings cards 302 back into the set and stack 300, a user may select and maintain selection of the settings card representation 350 corresponding thereto, which will add the settings card 302 back to the set and stack 300 and also remove the non-shown graphical indication 355 from the settings card representation 350.

Additionally, the plurality of settings card representations 350 depicted in the exemplary settings cards selection and arrangement functionality shown in FIG. 8 may also be depicted, or displayed, on the graphical user interfaces of FIGS. 5-6 such that, e.g., a user may use the plurality of settings card representations 350 to navigate the stack 301 of settings cards, a user may have additional visual indication where the presently-displayed settings card is located within the stack 301 of settings cards, etc. For example, a user may select (e.g., touch, click, etc.) a settings card representation 350 to display the settings card associated therewith. In other words, the settings card representation 350 may act as a "shortcut" that allows a user to "jump" to a particular settings card based on the selection of its settings card representation 350. Further, in one or more embodiments including the exemplary settings cards selection and arrangement functionality shown in FIG. 8 as well as this additional embodiment, an alphanumeric depiction may be depicted proximate each of the plurality of settings card representation 350 that includes an alphanumeric of the settings card representation 350 and the associated settings card. For example, the alphanumeric text "DIALYSIS FLUID" may be displayed proximate the settings card representation 350 that is associated with the dialysis fluid settings card. Still further, in one or more embodiments, a graphical depiction may be depicted proximate each of the plurality of settings card representation 350 that includes a graphic icon representing, or graphically conveying, which settings card is associated with, or corresponds to, the settings card representations 350. For example, a graphical icon representative of dialysis fluid may displayed within, or proximate, the settings card graphical representation 350 associated with, or corresponding to the dialysis fluid settings card.

The card set including all of the plurality settings cards 302, which may be displayed as stack 300, may be associated with a treatment cycle. In other words, all of the plurality of settings cards 302 of the card set and stack 300 displayed thereon may be associated with, or related to, a blood treatment. More specifically, the one or more settings displayed on the settings cards 302 for the card set and stack 300 may be settings that are part of a blood treatment performable by the exemplary blood treatment system. The exemplary systems and methods may further include additional cards grouped into additional card sets or card subsets that are not associated with, or related to, a blood treatment. For example, the exemplary systems and methods may include, or provide, a plurality of patient report cards grouped into a patient report set and plurality of system tools cards grouped into a system tool set. The patient report cards may include one or more settings and information elements related to one or more patients. The system tool cards may include one or more settings and information elements related to system setup, system maintenance or service, user preferences, calculator, etc.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:

1. An extracorporeal blood treatment system comprising:
   extracorporeal blood treatment apparatus comprising one or more pumps, one or more sensors, and one or more disposable elements for use in performing an extracorporeal blood treatment;
   a display apparatus comprising a graphical user interface, wherein the graphical user interface is configured to depict a plurality of settings cards; and
   a computing apparatus comprising one or more processors and operatively coupled to the extracorporeal blood treatment apparatus and the display apparatus, wherein the computing apparatus is configured to:
      provide a plurality of settings cards defining a card set using the one or more processors, wherein each settings card of the plurality of settings cards is configured to display real time extracorporeal blood treatment data and one or more settings related to one or more processes of the extracorporeal blood treatment system performable by the extracorporeal blood treatment apparatus, wherein the plurality of settings cards comprises a multi-settings card configured to display real time extracorporeal blood treatment data and a plurality of settings related to one or more processes of the extracorporeal blood treatment system performable by the extracorporeal blood treatment apparatus, wherein the plurality of settings cards comprises a single settings card configured to display real time extracorporeal blood treatment data and a single setting related to one or more processes of the extracorporeal blood treatment system performable by the extracorporeal blood treatment apparatus, wherein the settings cards are grouped into a plurality of card subsets, wherein each card subset comprises a plurality of settings cards that is less settings cards than the card set,
      display on the graphical user interface an all-settings graphical element and a plurality of card subset graphical elements using the one or more processors, wherein the all-settings graphical element is associated with the display of the card set, and wherein each card subset graphical element of the plurality of subset graphical elements is associated with the display of a different card subset of the plurality of card subsets,
      receive input from a user selecting the all-settings graphical element,
      display a stack of the plurality of settings cards of the card set in response to selection of the all-settings graphical element, wherein at least one settings card of the stack of the plurality of settings cards of the card set is presented at the forefront of the stack to the user while the remaining settings cards are obscured by the at least one settings card at the forefront such that only edges of the remaining settings cards are displayed,
      receive input from a user selecting one of the plurality of subset graphical elements,
      display a stack of the plurality of settings cards of the card subset associated with the selected card subset graphical element in response to selection thereof, wherein at least one settings card of the stack of the plurality of settings cards of the selected card subset is presented at the forefront of the stack to the user while the remaining settings cards are obscured by the at least one settings card at the forefront such that only edges of the remaining settings cards are displayed,
      present the multi-settings card displaying real time extracorporeal blood treatment data and the plurality of settings related to one or more processes of the extracorporeal blood treatment system performable by the extracorporeal blood treatment apparatus at the forefront of the stack,
      receive input from the user using the one or more settings of the presented multi-settings card to modify one or more settings of the plurality of settings of the multi-settings card related to one or more processes of the extracorporeal blood treatment system performable by the extracorporeal blood treatment apparatus,
      present the single settings card displaying real time extracorporeal blood treatment data and the single setting related to one or more processes of the extracorporeal blood treatment system performable by the extracorporeal blood treatment apparatus at the forefront of the stack,
      receive input from the user using the one or more settings of the presented single settings card to modify one or more settings of the single setting of the single settings card related to one or more processes of the extracorporeal blood treatment system performable by the extracorporeal blood treatment apparatus,
      change one or more settings of the one or more processes of the extracorporeal blood treatment system performable by the extracorporeal blood treatment apparatus using the one or more processors in response to the received input from the user modifying one or more settings of the presented multi-settings card and the presented single settings card, and perform an extracorporeal blood treatment using the extracorporeal blood treatment apparatus based on the changed one or more settings.

2. The system of claim 1, wherein the computing apparatus is further configured to:
    display on the graphical user interface a plurality of process feature graphical elements, wherein each process feature graphical element of the plurality of process feature graphical elements corresponds with a different process feature of the one or more processes of the extracorporeal blood treatment system performable by the extracorporeal blood treatment apparatus and is associated with the display of a single settings card of the plurality of settings cards;
    receive input from a user selecting a process feature graphical element of the plurality of process feature graphical elements to display the single settings card associated with the selected process feature graphical element;
    display the single settings card associated with the selected process feature graphical element in response to selection thereof;
    receive input from the user using the one or more settings of the displayed single settings card to modify one or more settings related to one or more processes of the extracorporeal blood treatment system performable by the extracorporeal blood treatment apparatus; and
    changing one or more settings of the one or more processes of the extracorporeal blood treatment system performable by the extracorporeal blood treatment apparatus in response to the received input from the user modifying one or more settings of the displayed single settings card.

3. The system of claim 1, wherein the stack of settings cards are graphically displayed as a three-dimensional deck of settings cards.

4. The system of claim 1, wherein the computing apparatus is further configured to change the one or more settings cards presented at the forefront of the stack in response to user interaction with the graphical user interface.

5. The system of claim 1, wherein the computing apparatus is further configured to change the order of the plurality of settings cards when displayed in a stack in response to user interaction with the graphical user interface.

6. The system of claim 1, wherein the computing apparatus is further configured to configure which settings cards of the plurality of settings cards are grouped into the plurality of card subsets in response to user interaction with the graphical user interface.

7. The system of claim 1, wherein each card subset of the plurality of card subsets is associated with a different chronological phase of a treatment process performable by the extracorporeal blood treatment system.

8. The system of claim 1, wherein the plurality of card subsets comprises a preparation card subset, wherein the preparation card subset comprises a treatment mode settings card, a setup settings card, and a priming settings card.

9. The system of claim 1, wherein the plurality of card subsets comprises a treatment card subset, wherein the treatment card subset comprises a blood settings card, an ultrafiltration settings card, a dialysis fluid settings card, and a treatment time settings card.

10. The system of claim 1, wherein the plurality of card subsets comprises a disinfection subset of settings cards.

11. The system of claim 1, wherein the computing apparatus is further configured to display at least one settings card of the plurality of settings cards in response to a status change of one or more processes being performed.

12. The system of claim 9, wherein the treatment time settings card is displayed in response to expiration of a treatment time period.

13. The system of claim 1, wherein the one or more settings of at least one settings cards of the plurality of settings cards is graphically expandable to display additional information with respect to the associated setting.

14. The system of claim 1, wherein the plurality of settings cards of the card set are associated with a treatment cycle, wherein the computing apparatus is further configured to provide a plurality of system configuration settings cards defining a system configuration card set different from the card set associated with a blood treatment.

15. The system of claim 1, wherein the display apparatus comprises a touchscreen.

16. A method for an extracorporeal blood treatment system comprising:
    providing extracorporeal blood treatment apparatus comprising one or more pumps, one or more sensors, and one or more disposable elements for use in performing an extracorporeal blood treatment;
    providing a graphical user interface on a display apparatus configured to depict a plurality of settings cards;
    providing a plurality of settings cards defining a card set, wherein each settings card of the plurality of settings cards is configured to display real time extracorporeal blood treatment data and one or more settings related to one or more processes of the extracorporeal blood treatment system performable by the extracorporeal blood treatment apparatus, wherein the plurality of settings cards comprises a multi-settings card configured to display real time extracorporeal blood treatment data and a plurality of settings related to one or more processes of the extracorporeal blood treatment system performable by the extracorporeal blood treatment apparatus, wherein the plurality of settings cards comprises a single settings card configured to display real time extracorporeal blood treatment data and a single setting related to one or more processes of the extracorporeal blood treatment system performable by the extracorporeal blood treatment apparatus, wherein the plurality of settings cards are grouped into a plurality of card subsets, wherein each card subset comprises a plurality of settings cards that is less settings cards than the card set;
    displaying on the graphical user interface an all-settings graphical element and a plurality of card subset graphical elements, wherein the all-settings graphical element is associated with the display of the card set, and wherein each card subset graphical element of the plurality of subset graphical elements is associated with the display of a different card subset of the plurality of card subsets;
    receiving input from a user selecting the all-settings graphical element;
    displaying a stack of the plurality of settings cards of the card set in response to selection of the all-settings graphical element, wherein at least one settings card of the stack of the plurality of settings cards of the card set is presented at the forefront of the stack to the user while the remaining settings cards are obscured by the at least one settings card at the forefront such that only edges of the remaining settings cards are displayed;
    receiving input from a user selecting one of the plurality of subset graphical elements;

displaying a stack of the plurality of settings cards of the card subset associated with the selected card subset graphical element in response to selection thereof, wherein at least one settings card of the stack of the plurality of settings cards of the selected card subset is presented at the forefront of the stack to the user while the remaining settings cards are obscured by the at least one settings card at the forefront such that only edges of the remaining settings cards are displayed;

presenting the multi-settings card displaying real time extracorporeal blood treatment data and the plurality of settings related to one or more processes of the extracorporeal blood treatment system performable by the extracorporeal blood treatment apparatus at the forefront of the stack;

receiving input from the user using the one or more settings of the presented multi-settings card to modify one or more settings of the plurality of settings of the multi-settings card related to one or more processes of the extracorporeal blood treatment system performable by the extracorporeal blood treatment apparatus;

presenting the single settings card displaying real time extracorporeal blood treatment data and the single setting related to one or more processes of the extracorporeal blood treatment system performable by the extracorporeal blood treatment apparatus at the forefront of the stack;

receiving input from the user using the one or more settings of the presented single settings card to modify one or more settings of the single setting of the single settings card related to one or more processes of the extracorporeal blood treatment system performable by the extracorporeal blood treatment apparatus;

changing one or more settings of the one or more processes of the extracorporeal blood treatment system performable by the extracorporeal blood treatment apparatus in response to the received input form the user modifying one or more settings of the presented multi-settings card and the presented single settings card; and performing an extracorporeal blood treatment using the extracorporeal blood treatment apparatus based on the changed one or more settings.

17. The method of claim 16, wherein the method further comprises:

displaying on the graphical user interface a plurality of process feature graphical elements, wherein each process feature graphical element of the plurality of process feature graphical elements corresponds with a different process feature of the one or more processes of the extracorporeal blood treatment system performable by the extracorporeal blood treatment apparatus and is associated with the display of a single settings card of the plurality of settings cards;

receiving input from a user selecting a process feature graphical element of the plurality of process feature graphical elements to display the single settings card associated with the selected process feature graphical element;

displaying the single settings card associated with the selected process feature graphical element in response to selection thereof;

receiving input from the user using the one or more settings of the displayed single settings card to modify one or more settings related to one or more processes of the extracorporeal blood treatment system performable by the extracorporeal blood treatment apparatus; and changing one or more settings of the one or more processes of the extracorporeal blood treatment system performable by the extracorporeal blood treatment apparatus in response to the received input from the user modifying one or more settings of the displayed single settings card.

18. The method of claim 16, wherein the stack of settings cards are graphically displayed as a three-dimensional deck of settings cards.

19. The method of claim 16, wherein the method further comprises changing the one or more settings cards presented at the forefront of the stack in response to user interaction with the graphical user interface.

20. The method of claim 16, wherein the method further comprises changing the order of the plurality of settings cards when displayed in a stack in response to user interaction with the graphical user interface.

21. The method of claim 16, wherein the method further comprises configuring which settings cards of the plurality of settings cards are grouped into the plurality of card subsets in response to user interaction with the graphical user interface.

22. The method of claim 16, wherein each card subset of the plurality of card subsets is associated with a different chronological phase of a treatment process performable by the extracorporeal blood treatment system.

23. The method of claim 16, wherein the plurality of card subsets comprises a preparation card subset, wherein the preparation card subset comprises a treatment mode settings card, a setup settings card, and a priming settings card.

24. The method of claim 16, wherein the plurality of card subsets comprises a treatment card subset, wherein the treatment card subset comprises a blood settings card, an ultrafiltration settings card, a dialysis fluid settings card, and a treatment time settings card.

25. The method of claim 16, wherein the plurality of card subsets comprises a disinfection subset of settings cards.

26. The method of claim 16, wherein the method further comprises displaying at least one settings card of the plurality of settings cards in response to a status change of one or more processes being performed.

27. The method of claim 24, wherein the treatment time settings card is displayed in response to expiration of a treatment time period.

28. The method of claim 16, wherein the one or more settings of at least one settings cards of the plurality of settings cards is graphically expandable to display additional information with respect to the associated setting.

29. The method of claim 16, wherein the plurality of settings cards of the card set are associated with a treatment cycle, wherein the computing apparatus is further configured to provide a plurality of system configuration settings cards defining a system configuration card set different from the card set associated with a blood treatment.

* * * * *